United States Patent
Downtown et al.

(10) Patent No.: US 8,835,362 B2
(45) Date of Patent: Sep. 16, 2014

(54) MODIFYING SINGLE PROTEINS (GPCR), LIGANDS, AND NANOPORE SURFACES TO CREATE BINDING-INDUCED MOLECULAR CHANGES OF PROTEIN-LIGAND COMPLEXES DETECTED IN NANOCHANNEL TRANSLOCATION

(71) Applicants: International Business Machines Corporation, Armonk, NY (US); The University of Melbourne, Parkville (AU); Florey Institute of Neuroscience & Mental Health, Parkville (AU)

(72) Inventors: Matthew Downtown, Victoria (AU); Natalie Gunn, Victoria (AU); Stefan Harrer, Hampton (AU); Priscilla Rogers, Victoria (AU); John Wagner, North Melbourne (AU); Ross Bathgate, Victoria (AU); Daniel James Scott, Victoria (AU); Stan Skafidas, Victoria (AU)

(73) Assignees: International Business Machines Corporation, Armonk, NY (US); The University of Melbourne (AU); Florey Institute of Neuroscience and Mental Health (AU)

( * ) Notice: Subject to any disclaimer, the term of this patent is extended or adjusted under 35 U.S.C. 154(b) by 0 days.

(21) Appl. No.: 13/727,090

(22) Filed: Dec. 26, 2012

(65) Prior Publication Data

US 2014/0179541 A1  Jun. 26, 2014

(51) Int. Cl.
  *C40B 30/10* (2006.01)
  *G01N 33/53* (2006.01)
(52) U.S. Cl.
  CPC .................. *G01N 33/5306* (2013.01)

USPC ........ 506/12; 435/285.2; 435/287.1; 204/451
(58) Field of Classification Search
  CPC .............................................. C40B 30/10
  USPC .............................................. 506/7
  See application file for complete search history.

(56) References Cited

U.S. PATENT DOCUMENTS

| 5,397,695 A | 3/1995 | Sutton et al. | |
| 6,428,959 B1 * | 8/2002 | Deamer | 435/6.18 |

(Continued)

OTHER PUBLICATIONS

I. Braslavsky, et al., "Sequence Information Can Be Obtained From Single DNA Molecules," Department of Applied Physics, California Institute of Technology; PNAS Apr. 1, 2003; vol. 100; No. 7; pp. 3960-3964.

(Continued)

*Primary Examiner* — Christopher M Gross
*Assistant Examiner* — Richard L Manteuffel
(74) *Attorney, Agent, or Firm* — Cantor Colburn LLP; Louis Percello

(57) ABSTRACT

A mechanism is provided for utilizing a nanodevice to distinguish molecules with different structure. The molecules translocate through or across a nanochannel filled with a electrolyte solution. An electrical signal through the nanochannel is measured for every translocation event. Inner surfaces of the nanochannel include a functional layer, which is a coating to functionalize the nanochannel, in which the functional layer is configured to interact with predetermined ones of the molecules during translocation events. It is determined that a combination of at least two different molecules is formed based on predetermined ones of the molecules interacting with the functional layer to change the electrical signal and/or change a translocation time for the translocation event.

13 Claims, 15 Drawing Sheets

(56) References Cited

U.S. PATENT DOCUMENTS

| | | | |
|---|---|---|---|
| 7,846,656 | B2 | 12/2010 | Mirzabekov et al. |
| 8,105,471 | B1 | 1/2012 | Han et al. |
| 8,232,105 | B1 | 7/2012 | Scott |
| 8,262,879 | B2 * | 9/2012 | Oliver .......................... 204/450 |
| 8,388,908 | B2 | 3/2013 | Blaga et al. |
| 8,481,334 | B1 | 7/2013 | Saul |
| 2004/0202994 | A1 | 10/2004 | Timperman |
| 2006/0275778 | A1 | 12/2006 | Wu et al. |
| 2008/0003571 | A1 | 1/2008 | McKernan et al. |
| 2008/0073512 | A1 | 3/2008 | Siuzdak et al. |
| 2009/0136948 | A1 * | 5/2009 | Han et al. .......................... 435/6 |
| 2009/0305273 | A1 | 12/2009 | Cao et al. |
| 2011/0053284 | A1 | 3/2011 | Meller et al. |
| 2012/0088315 | A1 | 4/2012 | Merelle et al. |
| 2013/0085680 | A1 | 4/2013 | Arlen et al. |

OTHER PUBLICATIONS

D. Branton, et al., "The Potential and Challenges of Nanopore Sequencing," Nature Biotechnology; 2008 Nature Publishing Group; pp. 1146-1153.

F. Collins, et al., "The Human Genome Project: Lessons from Large-Scale Biology," Apr. 11, 2003 vol. 300 Science www.sciencemag. org; pp. 286-290.

M. Fedurco, et al., "BTA, a Novel Reagent for DNA Attachment on Glass and Efficient Generation of Solid-Phase Amplified DNA Colonies," Nucleic Acids Research, 2006, vol. 34, No. 3; Published online Feb. 9, 2006; pp. 1-13.

S. Harrer, et al., "Electrochemical Characterization of Thin Film Electrodes Toward Developing a DNA Transistor," Langmuir Article 2010 American Chemical Society; Langmuir 2010, 26(24), pp. 19191-19198.

S. Harrer, et al., "Electrochemical Protection of Thin Film Electrodes in Solid State Nanopores," Nanotechnology 22 (2011) 275304 (6pp).

T. Harris, et al., "Single-Molecule DNA Sequencing of a Viral Genome," Science vol. 320, 106 (2008); pp. 106-109.

J. Kasianowicz, et al., "Characterization of Individual Polynucleotide Molecules Using a Membrane Channel," Proc. Natl. Acad. Sci. USA; vol. 93; pp. 13770-13773; Nov. 1996 Biophysics.

B. Luan, et al., "Tribological Effects on DNA Translocation in a Nanochannel Coated with a Self-Assembled Monolayer," J. Phys. Chem B., 2010, 114, pp. 17172-17176.

B. Luan, et al "Base-by-Base Ratcheting of Single Stranded DNA Through a Solid-State Nanopore," Physical Review Letters 104, 238103 (2010); pp. 238103-1-238103-4.

B. Luan, et al., "Control and Reversal of the Electrophoretic Force on DNA in a Charged Nanopore," J. Phys.: Condens. Matter 22 (2010) 454123 (5pp).

M. Margulies, et al., "Genome Sequencing in Microfabricated High-Density Picolitre Reactors," Nature vol. 437; Sep. 15, 2005 pp. 376-380.

S. Polonsky, et al., "Nanopore in Metal-Dielectric Sandwich for DNA Position Control," Applied Physics Letters 91, 153103 (2007); pp. 153103-1-153103-3.

F. Sanger, et al., "DNA Sequencing with Chain-Terminating Inhibitors," Proc. Natl. Acad. Sci. USA; vol. 74, No. 12; pp. 5463-5467; Dec. 1977 Biochemistry.

D. Scott, et al., "Direct Molecular Evolution of Detergent-Stable G Protein-Coupled Using Polymers Encapsulated Cells," 2012 Elsevier Ltd., J. Mol. Biol. (2013) 425, pp. 662-677.

J. Shendure, et al., "Accurate Multiplex Polony Sequencing of an Evolved Bacterial Genome," Science 309, 1728 (2005); pp. 1728-1732.

G. Turcatti, et al., "A New Class of Cleavable Fluorescent Nucleotides: Synthesis and Optimization as Reversible Terminators for DNA Sequencing by Synthesis," Nucleic Acids Research, 2008, vol. 36, No. 4; Published online Feb. 7, 2008; pp. 1-13.

D. Wang, et al., "DNA-Translocation Through a Solid State Nanopore coated with a Functionally Switchable Self-Assembled Monolayer," IBM T. J. Watson Research Center, Yorktown Heights, NY USA; 2012; pp. 1-18.

D. Wang, et al., "Regulating the Transport of DNA through Biofriendly Nanochannels in a Thin Solid Membrane," IBM Research at T.J. Watson Center, Yorktown Heights, NY USA; pp. 1-23.

E. Yusko, et al., "Developing Nanopores with Fluid Walls for Improved, Single-Molecule Biosensors," Abstract only Feb. 2012; 1 page.

Schoch et al., "Transport Phenomena in Nanofluidics," Reviews of Modern Physics, vol. 80, Jul.-Sep. 2008, 45 pages.

Bayley, Hagan et al.; Stochastic Sensors Inspired by Biology; Nature; vol. 413; p. 226-230; Sep. 13, 2001.

Hickman, James J., et al.; "Toward Orthogonal Self-Assembly of Redox Active Molecules on Pt and Au: Selective Reaction of Disulfide with Au and Isocyanide with Pt"; Langmuir; vol. 8; 357-359; 1992.

Li, Zhiyong, et al.; "Self-Assembly of Alkanethiol Molecules onto Platinum and Platinum Oxide Surfaces"; Langmuir; vol. 19; p. 6744-6749; 2003.

Martin, Benjamin R., et al; "Orthogonal Self-Assembly on Colloidal Gold-Platinum Nanorods"; Advanced Materials; vol. 11, No. 12; p. 1021-1025; 1999.

Miles, Benjamin N., et al.; "Single Molecule Sensing with Solid-State Nanopores: Novel Materials, Methods, and Applications"; Chemical Society Reviews; vol. 42; No. 1; p. 15-28; Jan. 7, 2013.

Petrovykh, Dmitri Y., et al.; Alkanethiols on Platinum: Multicomponent Self-Assembled Monolayers; Langmuir; vol. 22; p. 2578-2587; 2006.

Raillon, C., et al.; "Fast and Automatic Processing of Multi-Level Events in Nanopore Translocation Experiments"; Nanoscale; vol. 4; p. 4916-4924; 2012.

Randolph, S. J., et al.; "Focused, Nanoscale Electron-Beam-Induced Deposition and Etching"; Critical Reviews in Solid State and Materials Sciences; vol. 31; p. 55-89; 2006.

Tabard-Cossa, Vincent, et al.; "Noise Analysis and Reduction in Solid-State Nanopores"; Nanotechnology; vol. 18; p. 1-7; 2007.

Wei, Ruoshan, et al.; "Stochastic Sensing of Proteins with Receptor-Modified Solid-State Nanopores" Nature Nanotechnology; vol. 7; p. 257-263; Apr. 2012.

* cited by examiner

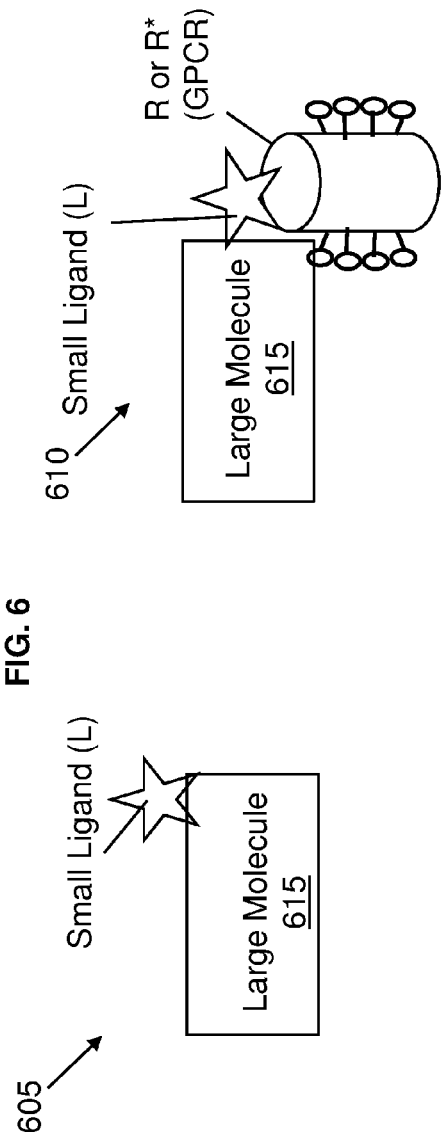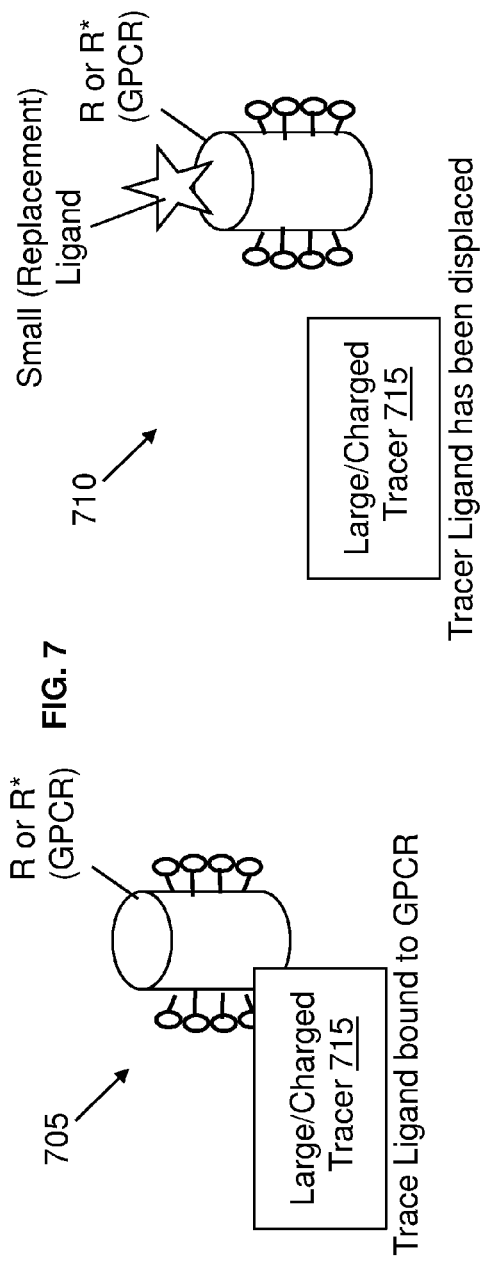

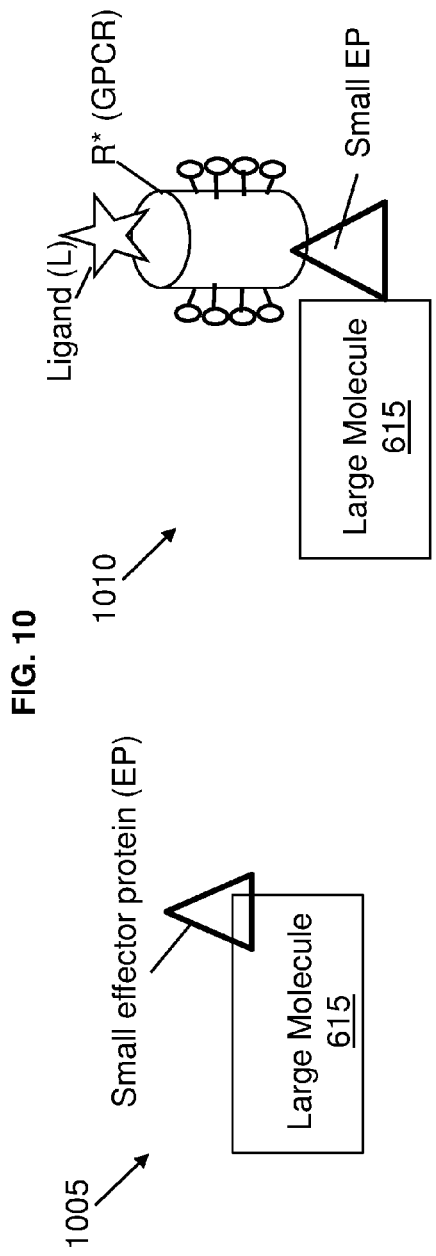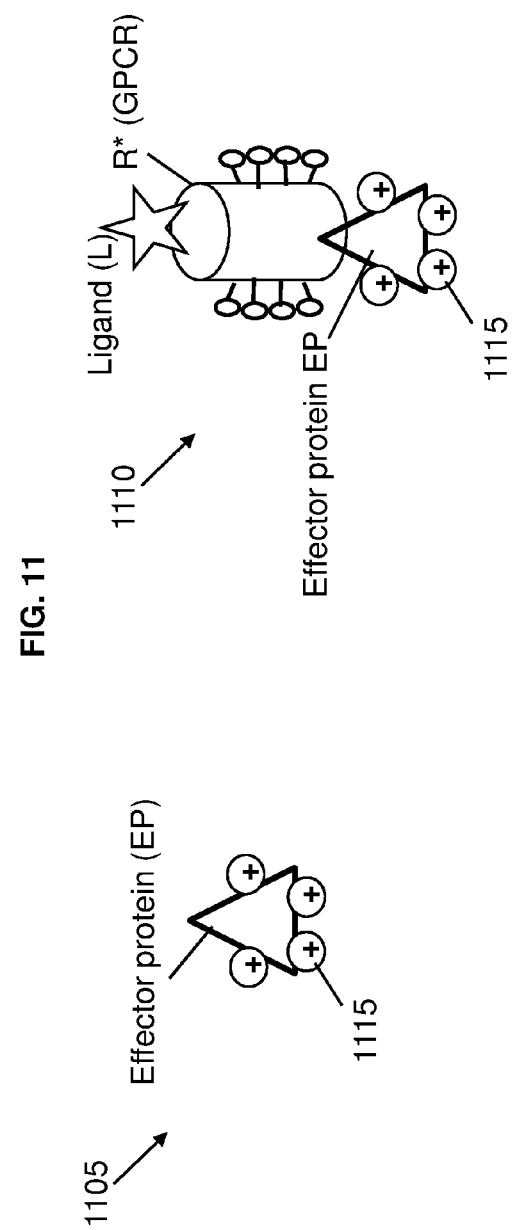
FIG. 10
FIG. 11

MODIFYING SINGLE PROTEINS (GPCR), LIGANDS, AND NANOPORE SURFACES TO CREATE BINDING-INDUCED MOLECULAR CHANGES OF PROTEIN-LIGAND COMPLEXES DETECTED IN NANOCHANNEL TRANSLOCATION

BACKGROUND

The present invention relates to drug screening, and more particularly, to analysis of protein binding reactions using a nanochannel-based chip.

In the fields of medicine, biotechnology, and pharmacology, drug discovery is the process by which new candidate medications are discovered. Historically, drugs were discovered through identifying the active ingredient from traditional remedies or by serendipitous discovery. Later, chemical libraries of synthetic small molecules, natural products, or extracts were screened in intact cells or whole organisms to identify substances that have a desirable therapeutic effect in a process known as classical pharmacology. Since sequencing of the human genome which allowed rapid cloning and synthesis of large quantities of purified proteins, it has become common practice to use high throughput screening of large compound libraries against isolated biological targets which are hypothesized to be disease modifying in a process known as reverse pharmacology. Hits from these screens are then tested in cells and then in animals for efficacy. Even more recently, scientists have been able to understand the shape of biological molecules at the atomic level, and to use that knowledge to design drug candidates (i.e., drug design).

Modern drug discovery involves the identification of screening hits, medicinal chemistry optimization of those hits to increase the affinity, selectivity (to reduce the potential of side effects), efficacy/potency, metabolic stability (to increase the half-life), and oral bioavailability. Once a compound that fulfills all of these requirements has been identified, it will begin the process of drug development prior to clinical trials.

Despite advances in technology and understanding of biological systems, drug discovery is still a lengthy, expensive, difficult, and inefficient process with a low rate of new therapeutic discovery. It is recognized that the research and development cost of each new molecular entity (NME) is approximately $1.8 billion (US).

With regard to drug targets, the definition of "target" itself is something argued within the pharmaceutical industry. Generally, the target is the naturally existing cellular or molecular structure involved in the pathology of interest that the drug-in-development is meant to act on. However, the distinction between a new and established target can be made without a full understanding of just what a target is. This distinction is typically made by pharmaceutical companies engaged in discovery and development of therapeutics. "Established targets" are those for which there is a good scientific understanding, supported by a lengthy publication history, of both how the target functions in normal physiology and how it is involved in human pathology. This does not imply that the mechanism of action of drugs that are thought to act through a particular established target is fully understood. Rather, "established" relates directly to the amount of background information available on a target, in particular functional information. The more such information is available, the less investment is (generally) required to develop a therapeutic directed against the target. The process of gathering such functional information is called "target validation" in pharmaceutical industry parlance. Established targets also include those that the pharmaceutical industry has had experience mounting drug discovery campaigns against in the past; such a history provides information on the chemical feasibility of developing a small molecular therapeutic against the target and can provide licensing opportunities and freedom-to-operate indicators with respect to small-molecule therapeutic candidates.

In general, "new targets" are all those targets that are not "established targets" but which have been or are the subject of drug discovery campaigns. These typically include newly discovered proteins, or proteins whose function has now become clear as a result of basic scientific research. The majority of targets currently selected for drug discovery efforts are proteins. Two classes predominate: G protein coupled receptors (or GPCRs) and protein kinases.

The process of finding a new drug against a chosen target for a particular disease usually involves high-throughput screening (HTS), wherein large libraries of chemicals are tested for their ability to modify the target. For example, if the target is a novel GPCR, compounds will be screened for their ability to inhibit or stimulate that receptor in cells (e.g., antagonist and agonist): if the target is a protein kinase, the chemicals will be tested for their ability to inhibit that kinase.

SUMMARY

According to an embodiment, a method for distinguishing molecules with different structure is provided. The method includes translocating the molecules through a nanochannel filled with an aqueous electrolyte solution and measuring an ionic current signal through the nanochannel for every translocation event. Inner surfaces of the nanochannel include a functional layer, which is a coating to functionalize the nanochannel, in which the functional layer is configured to interact with predetermined ones of the molecules during translocation events. The method includes determining that a combination of at least two different molecules is formed based on predetermined ones of the molecules interacting with the functional layer to at least one of change the ionic current signal and change a translocation time for the translocation event.

According to an embodiment, a system for distinguishing molecules with different structure is provided. A nanodevice includes a nanochannel connecting a first nanofluidic to a second nanofluidic reservoir, and the molecules translocate through the nanochannel filled with an aqueous electrolyte solution. A measuring device is connected to the nanodevice for making measurements, and the measuring device measures an ionic current signal through the nanochannel for every translocation event. Inner surfaces of the nanochannel include a functional layer, which is a coating to functionalize the nanochannel, and the functional layer is configured to interact with predetermined ones of the molecules during translocation events. The measurements determine that a combination of at least two different molecules is formed based on predetermined ones of the molecules interacting with the functional layer to at least one of change the ionic current signal and change a translocation time for the translocation event.

According to an embodiment, a method for distinguishing molecules with different structure is provided. The method includes translocating the molecules through a nanochannel filled with an electrolyte solution, and measuring an ionic current signal through the nanochannel for every translocation event. The method includes determining that at least two different molecules have combined into a combination based on at least one of a change in the ionic current signal and a change in translocation time for the translocation event. One of the molecules is a mutated protein.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 6 illustrates a small ligand chemically fused to a larger molecule and illustrates the combination of a GPCR bound to the small ligand chemically fused to the larger molecule, which may be utilized for any test solution as setup for biosensing testing via the nanodevice according to an embodiment.

FIG. 7 illustrates a receptor bound to a large and/or charged tracer ligand and illustrates a small ligand displacing the large/charged tracer ligand, which may be utilized for any test solution as setup for biosensing testing via the nanodevice according to an embodiment.

FIG. 10 illustrates a small effector protein fused to a large molecule to enhance the mass change of an effector protein and the large molecule combination, and illustrates a ligand that has bound to and activated a GPCR to allow the small effector protector fused to the large molecule to bind to the GPCR, which may be utilized for any test solution as setup for biosensing testing via the nanodevice according to an embodiment.

FIG. 11 illustrates an effector protein with charges, and illustrates that the effector protein with charges binds to the GPCR that is bound to and activated by the ligand, all of which may be utilized for any test solution as setup for biosensing testing via the nanodevice according to an embodiment.

DETAILED DESCRIPTION

Figure 1:
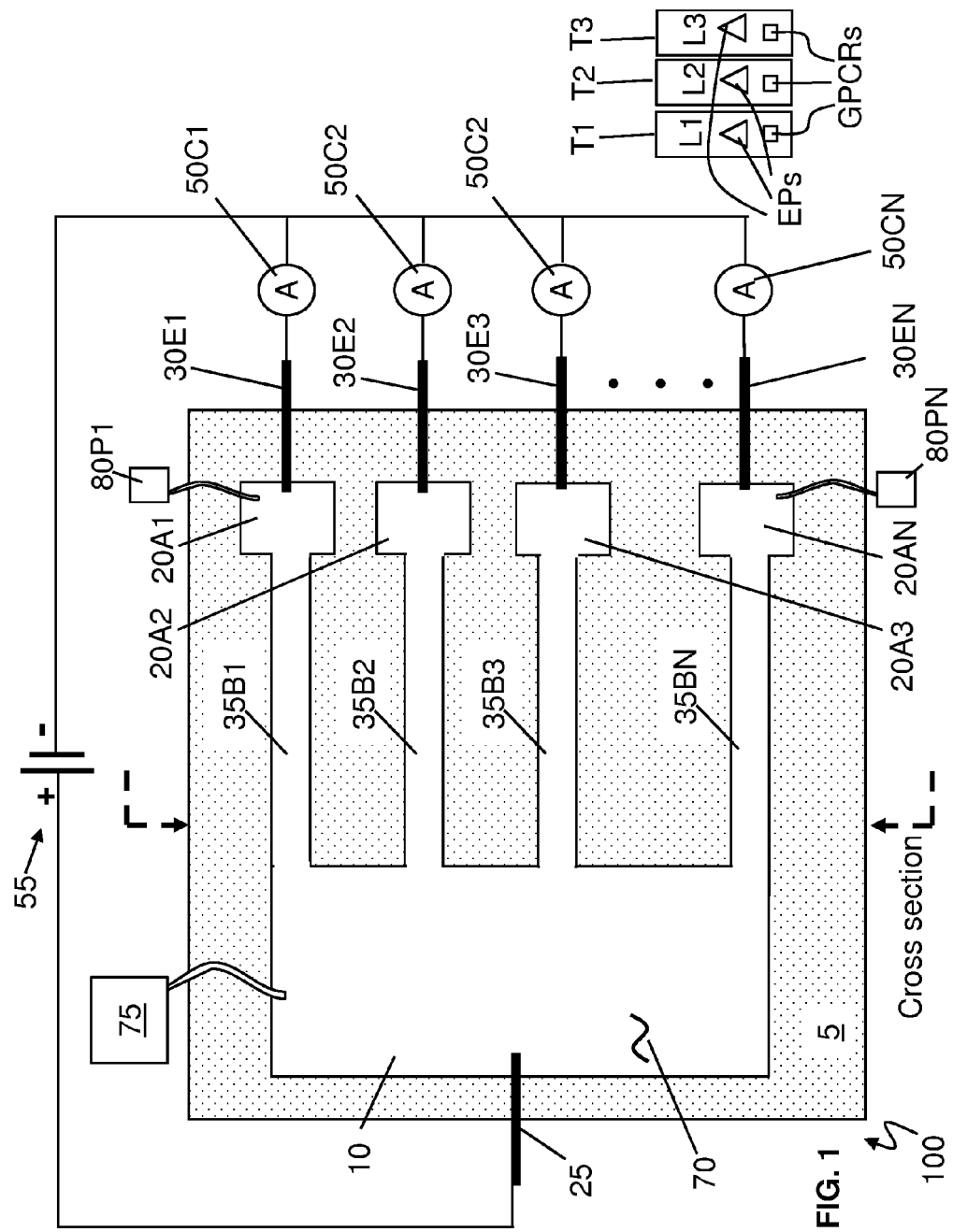
FIG. 1 is a schematic of a top view of a nanodevice according to an embodiment.

The present disclosure provides a novel drug screening technology that allows ultra-high throughput screening of GPCR binding and activation by compounds. This technique does not require incorporation of any custom-prepared biological cell-based assays into the test platform. Instead, the entire screening process may be performed in a nanofluidic chip, which is fabricated (in one case) using very large scale integration (VLSI) steps. Screening is accomplished by measuring the ionic currents through an array of wetted parallel nanochannels as G-Protein analogues, receptors, and agents (along with their various binding compounds) translocate through these nanochannels. The measured ionic currents have a distinct variation of the signal, and this variation in the ionic current corresponds to isolated G-Protein analogues, receptors, and agents as well as their various binding compounds (which translocate through these nanochannels). The nanofluidic chip itself may be used for all GPCR systems without further customization. The techniques disclosed herein represents a shift in how drug screening is performed because (1) they remove the difficult and slow step of incorporating cell-based assays into the testing scheme, and (2) they eliminate the need for creating a library of custom fluorescent markers by reducing the readout to an electrical measurement of single translocating molecules.

G-protein coupled receptors (GPCRs) are a superfamily of integral membrane proteins that transduce extracellular chemical and light signals into intracellular signaling pathways in all cell types. The large number of GPCR genes in the human genome underscores their importance in human health and disease: almost 800 GPCR genes, accounting for approximately 4% of the entire protein-coding genome, have been identified; and drugs targeting GPCRs account for the majority of best-selling drugs and about 40% of all prescription pharmaceuticals on the market. Notable examples include Zyprexa®, Clarinex®, Zantac®, and Zelnorm®.

There is broad consensus that GPCRs will remain at the hub of drug development activities for the foreseeable future. These proteins (i.e., GPCR) are active in just about every cell type and every organ system in humans, and present a wide range of opportunities as therapeutic targets in areas including cancer, cardiac dysfunction, diabetes, central nervous system disorders, obesity, inflammation and pain. Consequently, GPCRs are prominent components of pipelines in small and large drug companies alike, and many drug discovery firms focus exclusively on screening these receptors.

However, the path to novel GPCR-targeted medicines is not routine. Most GPCR-modulating drugs on the market were not initially targeted to a specific protein but were developed on the basis of functional activity observed in a biological assay; the fact that they activated or inhibited a GPCR specifically was only discovered later. In the post-Human-Genome-Project era, however, targets are the starting points for most drug discovery endeavors, and there is still much to be learned about GPCR function and selective modulation. Consequently, technologies designed specifically to tackle the GPCR challenge are blossoming. Most of these techniques, however, rely on cell assay-based approaches. Cell based assays need to be used because GPCRs, being integral membrane proteins, are extremely unstable when removed from the cell membrane, even when solubilized into detergent micelles. The instability of GPCRs in solution precludes their use in many biochemical assays and thus nanodevices.

However, in the present disclosure, the techniques combine two vastly different, technological platforms permitting a fundamentally different mode of measuring GPCR function that yields two opportunities: simplification of GPCR-modulating drug screening by decoupling the screening process from biological assay processing, and creation of an ultra-high-throughput, low-cost GPCR-modulating drug screening platform that dramatically improves industrial drug screening performance. By using the chip-based screening technique disclosed herein, these techniques significantly decrease cost and time of drug testing, thus also strongly catalyzing the discovery and understanding of new GPCR modulation mechanisms.

GPCRs exist at the interface of a cell's external and internal environments. When the matching natural ligand (which for the range of GPCRs could be an amine, ion, nucleoside, lipid, peptide, or protein) binds to a receptor's active site, this binding causes a conformational change in the protein to form its active state. This activates the G-protein coupled to the receptor on the cytosolic side of the membrane, leading to the activation of downstream processes.

Now, the state-of-the art drug screening technology is considered. The bread-and-butter of state-of-the-art GPCR high-throughput screening is cell-based assays. Tools such as fluorescent imaging plate readers (commonly referred to as FLIPRs) allow multi-well plate analysis of GPCR activation events, which give good hints of small-molecule drug leads. The idea for high-throughput cellular screening is to find a robust marker to monitor in cells overexpressing the GPCR of interest. Calcium ions are one popular choice: $Ca^{2+}$ is released from internal stores (e.g., endoplasmic reticulum) in cells upon activation of GPCRs coupled to $G\alpha_q$ proteins, which is one of the three main families of Ga proteins. The Brussels based company Euroscreen™, for instance, has developed the AequoScreen assay to fuel GPCR-based drug discovery programs. AequoScreen is based on a jellyfish-derived photoprotein called aequorin, which displays photo-activity proportional to $Ca^{2+}$ concentration. Screening a library against an array of GPCR-overexpressing cells mixed with aequorin provides a quantitative means of assessing a compound's ability to activate or inhibit a GPCR.

Besides the many GPCRs that function as basic receptors for sensory functions like sight and smell, which are not prime therapeutic targets, there are more than 300 other GPCRs available for drug discovery initiatives. About 200 of these (a portion of which account for currently marketed GPCR drug targets) have known natural ligands. The ligands of an additional 150 more nonsensory receptors identified as GPCRs by the Human Genome Project have not been found. These so-called orphan GPCRs have become a primary focus of many investigators and companies, because of the largely uncharted path of discovery they offer.

Typically, an initial goal is to deorphanize these GPCRs using high-throughput screening. Determining the endogenous ligand provides a first hint of function, structural cues for lead design, and a particular receptor-activating entity to antagonize.

In summary, state-of-the-art GPCR screening requires the following steps: (1) creating a reference cell line expressing the GPCR of interest; (2) establishing a cell based assay that measures the activation of the GPCR of interest, usually by measuring downstream effects of ligand mediated GPCR signaling; (3) application of the cell assay to drug discovery by treating the cell line with test ligands (agents); and (4) comparing the test results with the control cells. Thereby, the ligand (i.e., the drug agent to be tested) may either trigger GPCR signaling (activating the G-protein and thus a signaling process inside the cell) or block GPCR signaling (deactivating the GPCR and the signaling process inside the cell). For both cases, optical comparison of the ligand exposed GPCR cell line to the controls is the method to determine whether any potential drug hits have been identified. One problem with cell-based assays is that GPCR mediated signaling events can activate different cellular responses depending on the cell type used in a given assay. This can lead to potential drug molecules being missed in high throughput screens. Furthermore, the signals measured in most cell-based assays are derived from downstream signaling molecules that are removed from the GPCR protein by several members of a signaling cascade. Compounds may bypass the GPCR and activate the measured signal in a GPCR-independent way, leading to false positives. In addition, because the molecular function of the GPCR is not specifically being assayed, any subtle effects elicited on the GPCR by certain compounds will be invisible in the assay readout.

Now, turning to the figures, FIG. 1 is a schematic, which illustrates a top view of a nanodevice 100 according to an embodiment. The nanodevice 100 is an integrated biosensor design utilized for drug screening as discussed herein.

The nanodevice 100 has a substrate 5 which may be silicon (e.g., of a silicon wafer). The nanodevice 100 has a joint reservoir 10 connected to a reference electrode 25.

Individual reservoirs 20A1, 20A2, 20A3 through 20An are respectively connected to their own individual electrode 30E1, 30E2, 30E3 through 30En. The individual reservoirs 20A1-20An may be generally referred to as individual reservoirs 20, and the individual electrodes 30E1-30En may be generally referred to as individual electrodes 30.

Nanochannels 35A1, 35A2, 35A3 through 35An respectively connect the individual reservoirs 20A1, 20A2, 20A3 through 20An to the joint reservoir 10. The nanochannels 35A1, 35A2, 35A3 through 35An may be generally referred to as nanochannels 35. The nanochannels 35 may also be referred to as nanopores. The nanochannels 35 may have a diameter between 1 nanometer (nm) and 100 nm.

The joint reservoir 10, the nanochannels 35, and the individual reservoirs 20 are initially wetted (filled) with an aqueous electrolyte solution 70 (e.g., such as a combination of ethanol and water).

The reference electrode 25 is connected to one end of a voltage source 55 and the individual electrodes 30E1-30En are connected to the other end through their respective ammeters 50C1, 50C2, 50C3 through 50Cn (generally referred to as ammeters 50). The same potential (e.g., voltage V of voltage source 55) is applied between the reference electrode 25 and the individual electrodes 30 resulting in the induced background ionic current (i.e., without G-proteins and ligands) through the nanochannels 35 which is measured via respective ammeters 50C1-50Cn. When no test solutions are added to the electrolyte solution 70 each ammeter 50 measures the same (or approximately the same) amount current. For example, when the voltage V is applied by the voltage source 55, ionic current flows (from a conventional current flow direction) from the voltage source 55, through reference electrode 25, into the joint reservoir 10, through nanochannel 35B1, into individual reservoir 20A1, through electrode 30E1, ammeter 50C1 (where the ionic current for this particular nanochannel 35B1 is measured, e.g., in nanoamps (nA)), and back to voltage source 55. Although described for nanochannel 35B1, this ionic current flow occurs (as discussed above) for each nanochannel 35 to be respectively measured by connected ammeters 50.

As noted above, when the voltage V is applied (by the voltage source 55) between the reference electrode 25 and the individual electrodes 30 along each nanochannel 35, the ionic (background) current I flowing through the nanochannels 35 is measured (via respective ammeters 50C1) as the same value/amount for each nanochannel 35.

Figure 14:
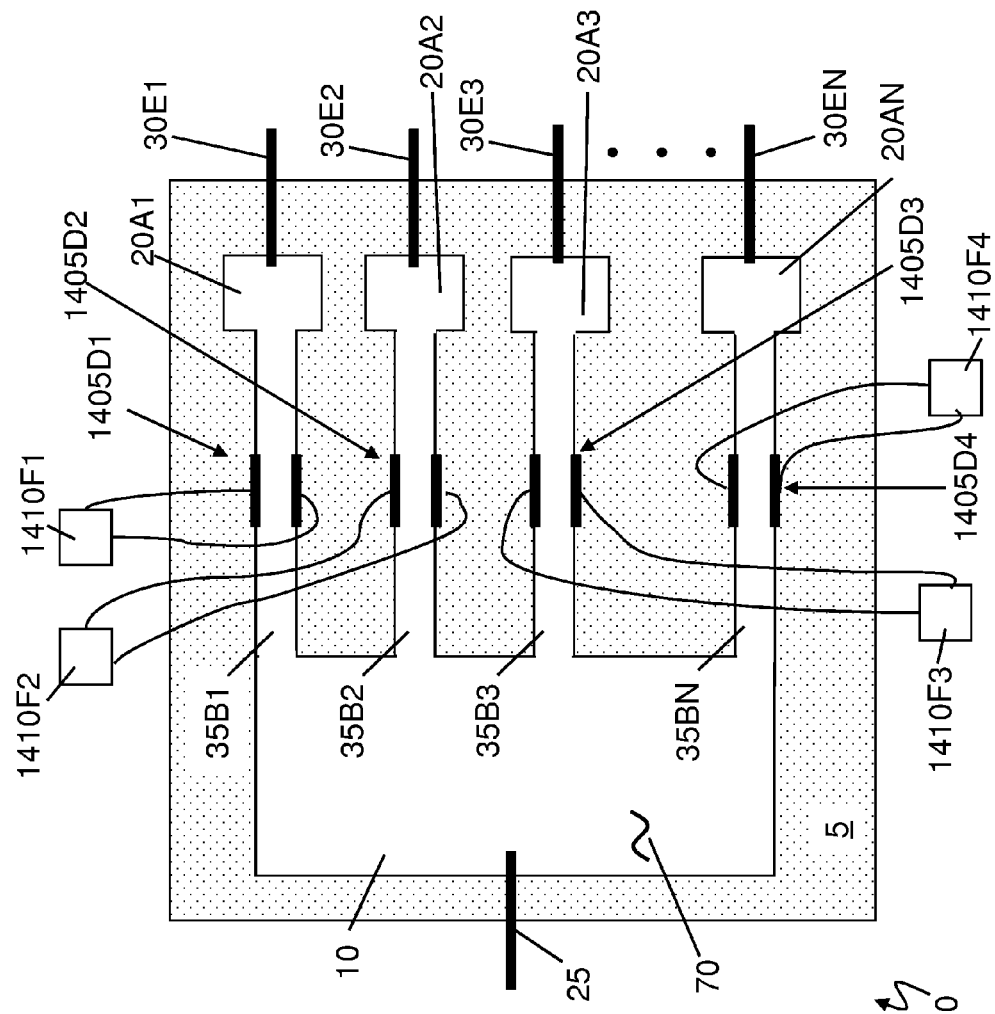
FIG. 14 is a schematic of the nanodevice with capacitive sensing via embedded electrode pairs in nanochannels according to an embodiment.
Figure 17:
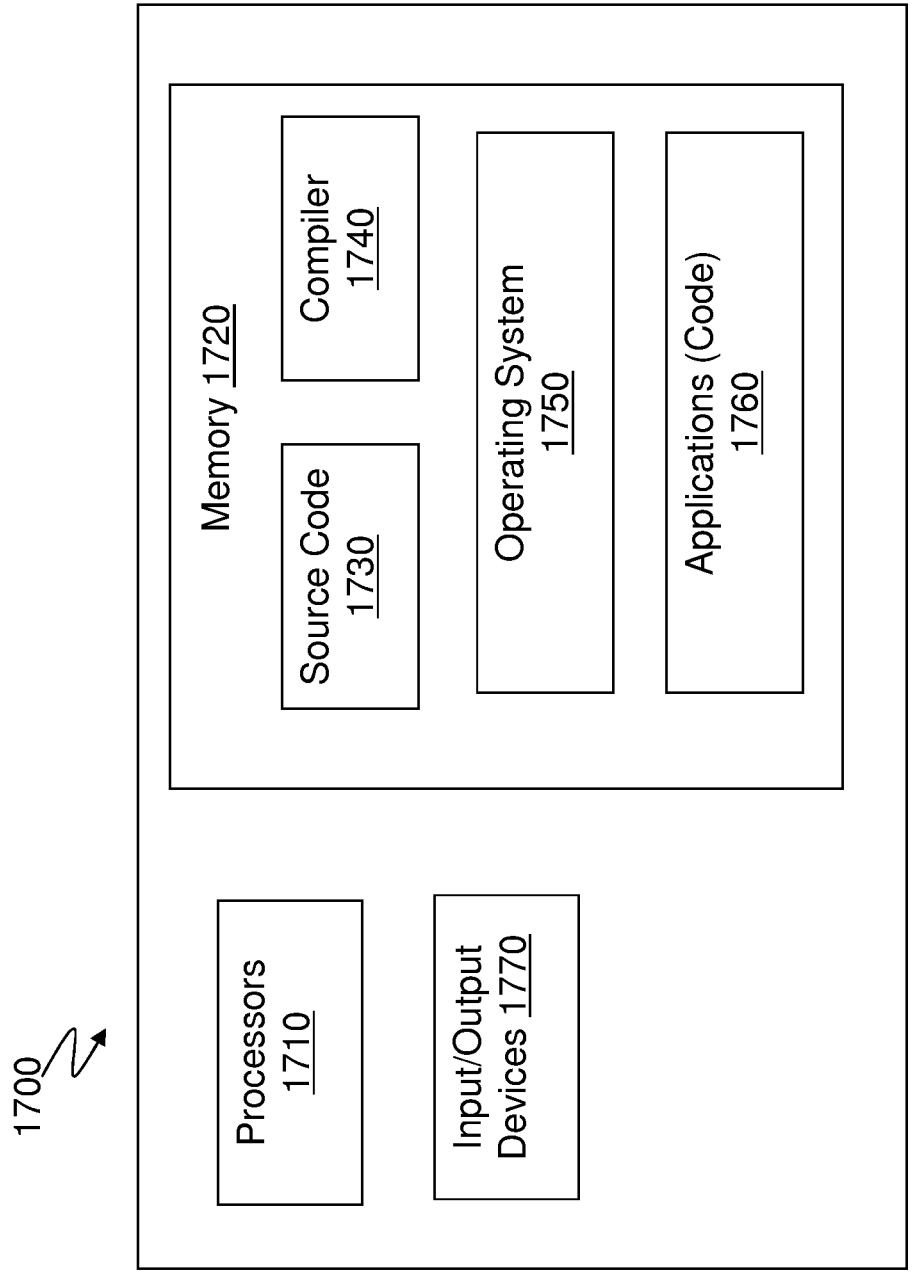
FIG. 17 illustrates an example of a computer having capabilities, which may be included in and connected to embodiments.

Note that a computer 1700 having a software application 1760 (as shown in FIG. 17) may include, connect to, and/or implement the functions of the voltage source 55, each individual ammeter 50, and each individual capacitance meter 1410 (as shown in FIG. 14) to record and graphically display each individual measurement during test runs. The software application 1760 of the computer 1700 analyzes the drops (and increases) in ionic current for each individual nanochannel 35, along with the time duration of the ionic current drops and increases for each translocation event, to determine the behavior of the molecules being tested (as discussed herein).

For drug screening tests, test solutions (e.g., test solutions T1, T2, and T3) containing GPCRs and various ligands to be tested are added to the system (i.e., added to the electrolyte solution 70) at either the individual reservoirs 20 (A1, A2 through AN) or the joint reservoir 10. FIGS. 4, 5, 6, 7, 10, 11, and 12 illustrate various test solutions T1, T2, T3, etc., which can be utilized as test runs for testing whether GPCR (proteins) combine with the tested ligand via the nanodevice 100. As all different compounds/molecules of the test solutions translocate (i.e., move) through the respective nanochannels 35 the ionic current signal is monitored at each individual electrode 20A1-20An via respective ammeters 50C1-50Cn (and/or computer 1700).

Depending on whether ligands and GPCRs were binding in a specific test solution (i.e., representing a particular drug), a conformational change of the GPCR molecule is induced. The average number of bound GPCR-ligand compounds in relation to the unbound GPCR and ligand molecules can be determined for every test solution by performing a statistical analysis of the translocation data. The solution (e.g., test solution T1, T2, and T3) with the most bound GPCR-ligand translocation events contains the most effective ligand, i.e., the most effective drug. A ligand bound to a protein (GPCR) may be referred to at times as a GPCR-ligand complex, protein-ligand complex, GPCR-ligand compound, protein-ligand compound, GPCR-ligand combination, protein-ligand combination, etc., as understood by one skilled in the art.

Several test solutions, such as test solutions T1, T2, T3, through TN with each containing the same GPCRs but different ligands (i.e. test agents) L1, L2, L3 through LN (all mixed in the electrolyte solution 70), may be prepared. The drug screening may occur according to the following scheme. The test solution T1 is inserted/pumped into the joint reservoir 10 for testing the ligands L1 with via a pump 75 (e.g., a syringe or motorized pump) communicatively connected to the joint reservoir 10. After the test solution T1 is pumped into the joint reservoir 10 via the pump 75, the species present in the joint reservoir 10 are now GPCRs, ligands L1, and potentially ligands L1 bound to activated GPCRs, thereby creating a new species GPCR-L1 activated (compound) having a different conformational state than separate GPCR and L1. Each of these compounds (GPCRs, ligands L1, and ligands L1 bound to activated GPCRs (i.e., GPCR-ligand)) are now dragged (i.e., translocated) through each nanochannel 35 (e.g., there may be 10, 20, 30, and/or 100 different nanochannels 35 also in one case there may be 1000 different nanochannels 35 in the nanodevice 100) by the background electrolyte flow (e.g., generated by the voltage applied by the voltage source 55). The ionic current signals through the nanochannels 35 are monitored at electrodes 30E1, 30E2, 30E3 through 30En via the respective ammeters 50C1, 50C2, 50C3 through 50CN during the test run. Measured translocation events through each nanochannel 35 show three different electrical signals. For example, the longest translocation time may indicate GPCR-ligand activated translocation events, the shortest translocation time may reflect unbound ligand L1 translocation events, and medium translocation time may indicate unbound GPCR translocation events (another scenario may be based on the current drop). Based on translocation experiments performed with 2 kbp (kilo base pair is a unit of size and length) single-stranded DNA translocation numbers for GPCRs are expected to be in the 1000 events/min·channel range, which is event per minute per channel. A chip (such as the nanodevice 100) comprising 100 nanochannels therefore yields approximately 106 translocation events within a 1 min testing time. This allows a statistically meaningful data analysis (e.g., performed by the software application 1760 on the computer 1700) on the translocation time distributions (i.e., respective translocation times for all translocation events per nanochannel 35 for a test run) for the test solution T1. The chip of the nanodevice 100 is flushed with a pure electrolyte solution (e.g., mixture of ethanol and water) to remove the test solution T1 from the nanochannels 35, the joint reservoir 10, and individual reservoirs 20, so that the same testing procedure is performed using test solution T2, T3 through TN.

For increased parallelization of screening different candidate drugs, test solutions T1 through to TN may be added to separate and individual reservoirs 20A1 through AN at the same time (i.e., each individual reservoir would consist of a different test solution). The test solution could be added to the individual reservoirs as either discrete or continuous (via a pump) fluid samples. Following the same procedure aforementioned, the only difference would be that the joint reservoir 10 would collect the multiple test solutions. This method would allow simultaneous testing of different drugs, in which electric measurements described above would provide information on the most effective candidate drug.

In a straight-forward comparative data analysis (which can be determined by application 1760 of the computer 1700), the test solution from the range tested (e.g., out of test solution T1, T2, and T3, in this example) showing the longest translocation events points to the highest concentration of GPCR-ligand activated, and therefore to the most effective ligand (i.e., drug such as tested ligand L1, L2, or L3 all being compared) for the tested GPCR. There are many different types of ligands. For example, ligands can be agonists and antagonist. Agonist ligands activate a receptor such as the GPCR. Antagonist ligands inhibit the receptor.

Once the various test solutions (such as test solutions T1, T2, T3 through TN) are generated, the testing procedure is completely automated using the very same chip with the nanodevice 100 until all of the test runs are completed. A test run corresponds to individually testing a single test solution in the nanodevice 100.

There can be an overall throughput per chip of 1 ligand/90 s (including 30 seconds flushing time per test run to then add the next test solution). Data analysis is readily available after the complete test series (i.e., testing all of the test solutions T1, T2, and T3) is completed. By varying the number of nanochannels 35 per chip within the nanodevice 100 and varying the number of chips per platform, throughput can easily be scaled up significantly. A platform may have 1-N amount of chips with the nanodevice 100.

The current state-of-the art cell-based screening techniques need to be thoroughly tested and validated before being applied to high-throughput screening platforms because of the expense involved in producing enough cells and compounds for the 100 mL (microliter) per sample scale needed. Furthermore, because downstream cell signaling events are monitored, false negatives are extremely common.

By screening GPCRs on the molecular level, the present disclosure not only simplifies drug screening but also reduces the cost of screening by reducing the scale of each data point to the nano level.

In the present disclosure, there are various alternatives and features for obtaining a translocation fingerprint by monitoring the ionic current signal through the nanochannel 35 (which may be combined in any manner). For example, the nanochannels 35 can be made so small and their diameter controlled so precisely (e.g., with 1-nm-precision) so that GPCR-LN$_{activated}$ (where N represents any particular ligand, such as ligand L1, L2, L3, L4, etc.) does not fit through the nanochannel 35 any more while the unbound GPCR and LN fit through nanochannels 35. In that case, there are not any translocation events for (the bound) GPCR-LN$_{activated}$ because this species would be filtered out to stay in joint reservoir 10 (and not pass through the nanochannel 35). For various test solutions TX (i.e., there can be multiple test solutions T1-TN) in which all the test solutions TX have the same initial concentrations of GPCR and LN, the ligand LN that causes the fewest translocation events (i.e., the fewest drops in ionic current, and/or the fewest occurrences of amplitude changes for relatively long time duration as measured by the ammeter 50 connected to the computer 1700) is the test solution that triggered the most GPCR-LN$_{activated}$ binding events and thus is the most effective agonist ligand; in this case, there is no need to further characterize these translocation events by measuring translocation times (e.g., time duration in the nanochannel 35, etc.). The nanodevice 100 on the chip would have to be flushed with a pressure gradient (e.g., using pumps 80P1 through 80PN (generally referred to as pump 80), where each nanochannel 35 is respectively connected to its own pump 80) pointing from the individual reservoirs towards the joint reservoir to get rid of potential GPCR-LN$_{activated}$ before the next test solution is inserted/pumped into the nanodevice 100 on the chip.

Figure 8:
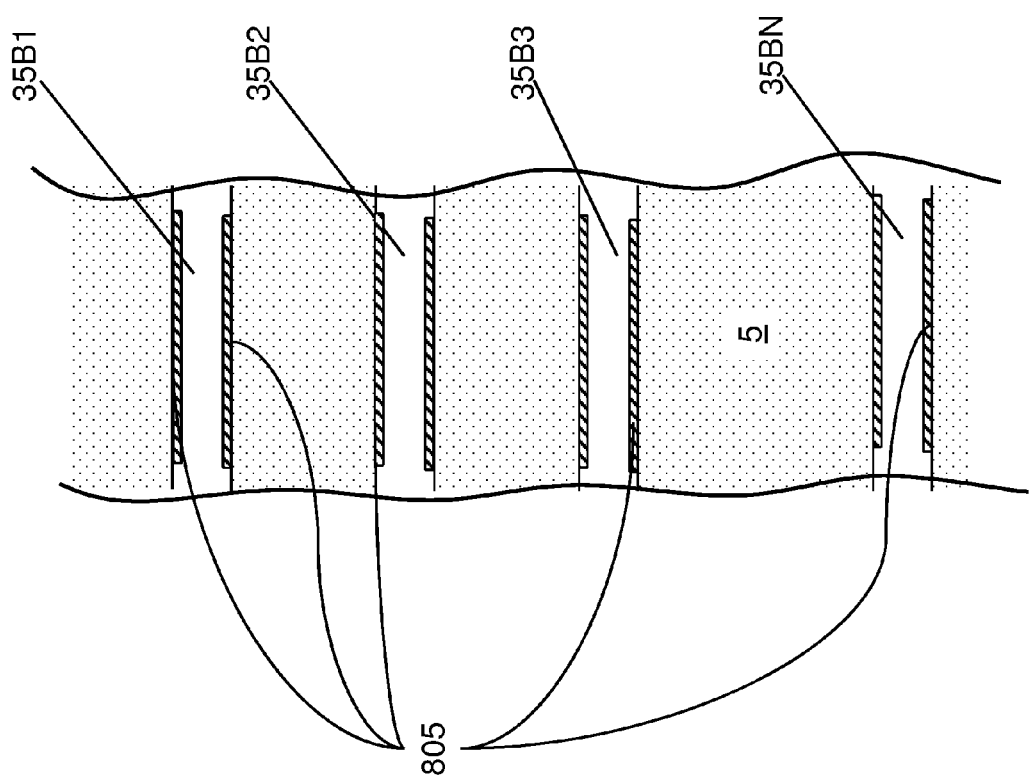
FIG. 8 illustrates nanochannels of the nanodevice coated with a coating to selectively interact with desired molecules in test solutions by attaching/bonding to the desired molecules translocating through the nanochannels according to an embodiment.

Also, by monitoring the ionic current signal (via ammeters 50) through the nanochannel 35, nanochannels 35 may be coated (as shown in FIG. 8) with GPCR on the inside of the nanochannel 35. Test solutions T1 through TN in this case (which are respectively pumped into the joint reservoir 10 via pump 75), contain G-protein analogues and ligands. The ligands and G-proteins translocate through the nanochannels 35 in their unbound states. G protein analogue, binding to the receptor inside the nanochannels 35 but not attracting the ligand, decreases the ionic background current (measured by respective ammeters 50) but still allows translocations of ligands through the nanochannel 35. Ligands binding to GPCRs inside the nanochannel and activating the GPCR, block the respective nanochannel 35, and practically no translocations are observed any more. In this scenario, the operator flushes the receptor-coated nanochannel 35 with G-protein analogues and a selection of subsequently added ligands (i.e., the next ligand to be tested in the next test solution) without having to flush the nanodevice 100 before adding each new ligand. As soon as the ionic pore current decreases substantially (when monitoring and recording the ionic current via the respective ammeters 50 and computer 1700) the most effective ligand has just been added (which may be any one of ligands L1, L2, L3, etc., being consecutively tested). This testing variation requires custom nanochannel 35 coating before the test run but eliminates the need for measuring translocation fingerprints. As shown in nanodevice 200 of FIG. 2, the nanodevice 100 on the chip only needs to have two joint reservoirs 10 and 20A1 combining all ends and openings of each nanochannel 35 (that is each of the individual reservoirs 20A1 through 20An are connected), and no individual channel measurements (via multiple ammeters 50) are necessary (because a single ammeter 50 can be utilized). Furthermore, the number of nanochannels 35 should be massively parallel (e.g., channel number $>10^6$) so that the combined ionic current through all nanochannels 35 in parallel is measured via the ammeter 50C1. As soon as this combined current signal drops significantly (e.g., drops by one-third, one-quarter, one-half, and/or more), a statistically meaningful statement can be made about the number of nanochannels 35 being blocked by activated GPCR-LN$_{activated}$ and hence about the most effective ligand causing this drop in measured ionic current (for the particular test solution being tested). In other words, the presently tested ligand (e.g., ligand L5) is the most effective agonist ligand (i.e., the effective drug candidate) based on this drop in the ionic current as measured by the single ammeter 50C1 for the nanodevice 200.

Figure 3:
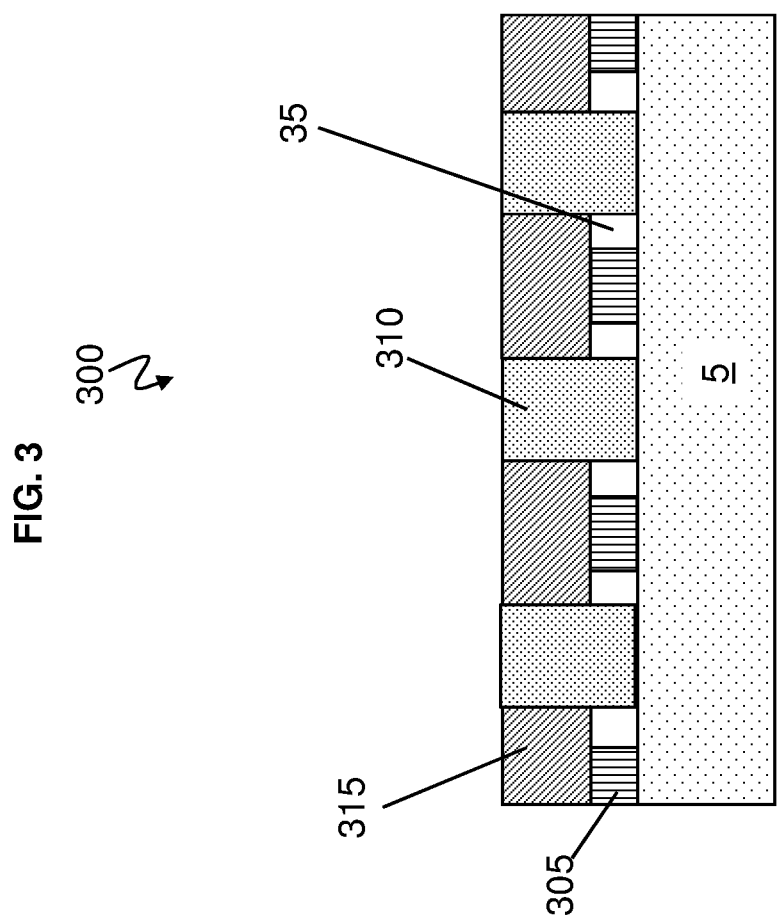
FIG. 3 is a schematic of a cross-sectional view of the nanodevice according to an embodiment.

FIG. 3 illustrates a cross-sectional view 300 of the nanodevice 100 and 200 according to an embodiment. The cross-sectional view 300 of nanodevice 100 and 200 includes the substrate 5 which may be silicon (e.g., a silicon wafer). Dielectric layer 305 is formed on top of the substrate 5 and dielectric layer 315 is formed on top of the dielectric layer 305. A dielectric fill layer 310 is formed on top of the substrate 5, and abuts the sides of the dielectric layer 315, thus forming the nanochannels 35.

Figure 4:
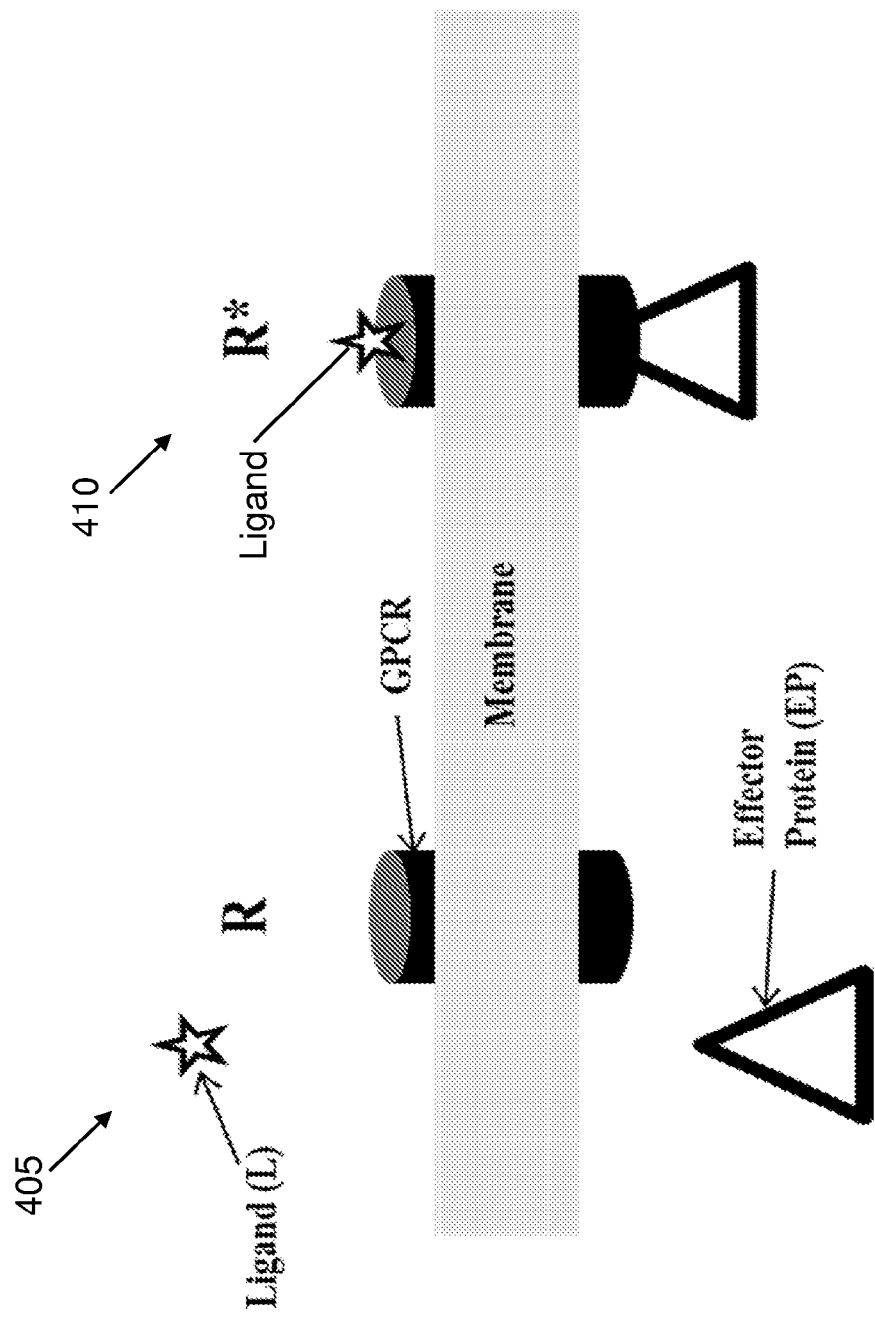
FIG. 4 illustrates components (molecules) of GPCR based signalling, which may be utilized in any test solution as a setup for biosensing testing via the nanodevice according to an embodiment.

The protein such as the G-protein (GPCR) is activated when it binds an agonist ligand, and this binding indicates that the ligand is a successful drug candidate. Specific examples of how to measure GPCR activation (which means that the agonist ligand has bound to the GPCR) with nanodevice 100 (and/or nanodevice 200) are provided below. For a prepared test solution (e.g., test solution T1, T2, T3), FIG. 4 illustrates the components (molecules) of GPCR based signalling which may be in any desired test solution T1 through TN as a setup for biosensing testing via the nanodevice 100 as discussed herein. GPCRs are located in the cell membrane in an unbound, inactive state (R). Binding of an agonist ligand (L) to the receptor (GPCR) results in the receptor (GPCR) moving into an activated conformation (R*), where the GPCR is able to bind to effector proteins (EPs) located inside the cell. R is utilized to represent the unbound inactive GPCR, and R* is utilized to represent the activated GPCR (where binding to the ligand activates the GPCR). In view 405, the unbound inactive GPCR (R) is not bound to or activated by the ligand, and is not bound to the effector protein (EP). In view 410, the GPCR (R*) is bound to and activated by the ligand, and is also bound to the effector protein (EP).

Figure 5:
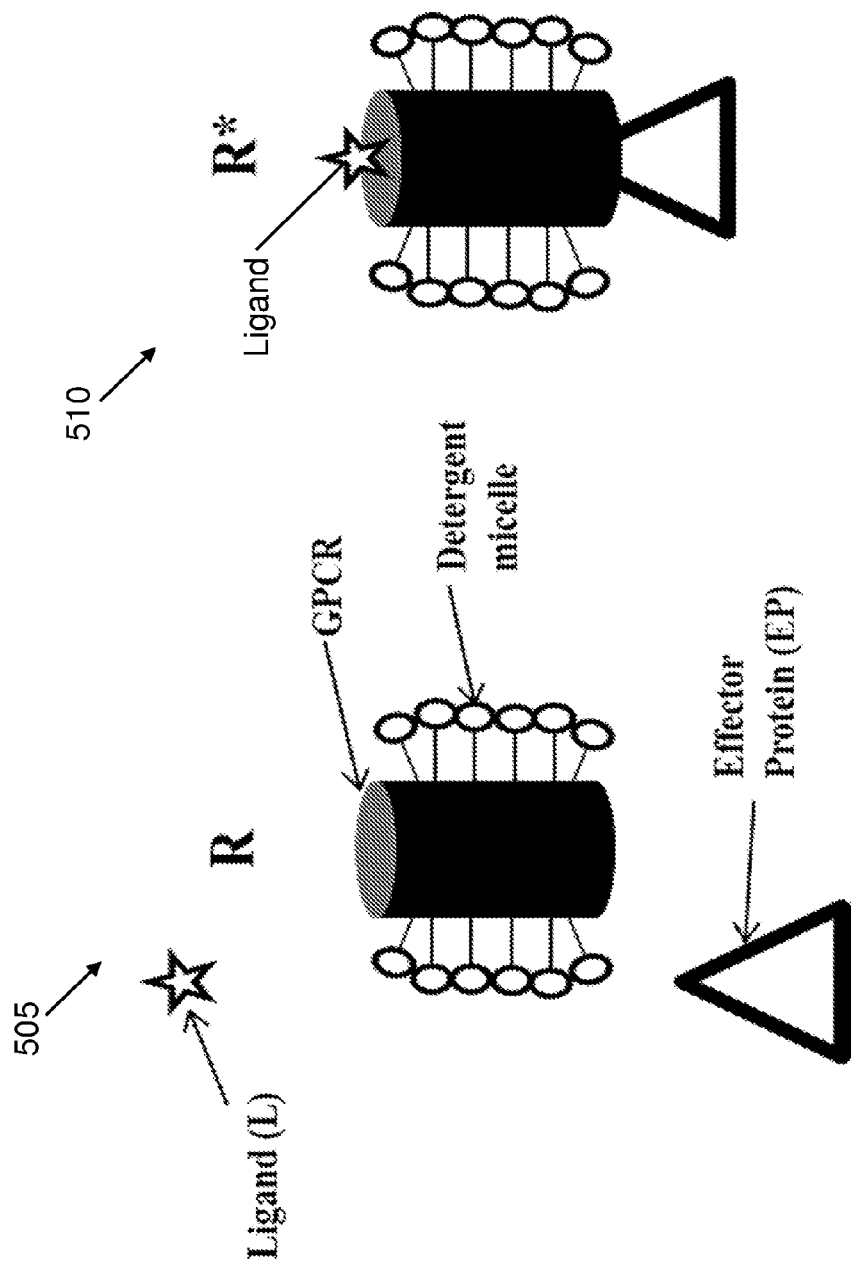
FIG. 5 illustrates binding of detergent solubilised GPCR proteins to ligands and effector proteins, which may be utilized for any test solution as setup for biosensing testing via the nanodevice according to an embodiment.

FIG. 5 illustrates binding of detergent solubilized GPCR proteins to ligands and effector proteins, which may be utilized for any test solutions T1 through TN as setup for biosensing testing via the nanodevice 100 as discussed herein. A stabilized GPCR can be solubilised out of the membrane (shown in FIG. 4) into detergent micelles by treating GPCR expressing cells with a detergent solution with or without some form of mechanical or ultrasonic disruption, which breaks the cells open. Specific detergents need to be used that attack the cell membrane, solubilizing the proteins in the membrane, such as GPCRs, by encasing them in detergent micelles that mimic the membrane bilayer Detergent solubilized GPCRs can then be purified from the solubilized cell mixture using standard biochemical techniques such as affinity chromatography and gel filtration. Detergent solubilized GPCRs may be referred to as mutated protein. As in FIG. 4, the GPCR can exist in an inactive state (R), but upon binding an agonist ligand (L) to the GPCR, the receptor (GPCR) undergoes a conformational change into an activated state (R*), upon which the GPCR is able to bind to effector proteins (EPs). In view 505, the unbound inactive GPCR (R) is not bound to or activated by the ligand, and is not bound to the effector protein (EP). In view 510, the GPCR (R*) is bound to and activated by the ligand, and is also bound to the effector protein (EP).

By measuring current changes (via respective ammeters 50) and pore retention times (the time duration of the (change in) ionic current while the tested molecule is in the nanochannel 35), the computer 1700 (and/or operator) is able to determine if a particular translocating receptor (GPCR) is (1) in an unbound, inactive state (R), (2) is bound to a ligand in an inactive state (RL), (3) bound to a ligand in an active state (R*L), and/or (4) bound to a ligand in an unbound, activated state (R*).

Measuring R Versus R*:

Further discussion is now provided regarding measuring a translocating receptor (GPCR) in an unbound, inactive state (R) versus measuring the translocating receptor (GPCR) bound to a ligand in an inactive state (RL) via the nanodevice 100 as discussed herein. R designates the unbound inactive receptor (e.g., GPCR). RL designates the inactive receptor bound to a ligand, such as the GPCR bound to the ligand (i.e., RL complex or combination).

In the case that the ligand (L) being used is a large molecule (e.g., >10 kDa) (e.g., in any of the test solutions T1, T2, and/or T3), the change in mass of the RL complex (e.g., the GPCR bound to the ligand) is large enough that a significant change in retention time (in the nanochannel 35), compared with R (e.g., the unbound inactive GPCR), is observed. Retention time is the same as the time duration for the change in ionic current in the nanochannel 35 (such as a drop in ionic current), during the translocation event. The Dalton (Da) or more conveniently the kDa (kiloDalton) is a unit for molecular mass or mass as understood by one skilled in the art. For example, when voltage is supplied by the voltage source 55 to the electrodes 25 and 30, the ammeter 50 (alone and/or implemented in the computer 1700) measures a longer time duration (in the nanochannel 35) for the change in ionic current (e.g., decrease/drop) for the RL complex/combination (e.g., GPCR bound to a ligand having a large molecular weight such as greater than 10 kDa), as compared to a change (e.g., decrease/drop) in ionic current for R (the unbound GPCR) and/or the ligand (L) when traveling through the nanochannel 35.

If a given receptor (e.g., GPCR) binds to small ligands (e.g., less than 5 kDa in molecular weight or less than 2 kDa), the mass difference between R and RL may be too small to resolve differences in retention time. In this case, the small ligand (e.g., less than 10 kDa) may be chemically fused to a larger molecule (e.g., albumin), to increase the mass of the ligand so that the retention time of RL is significantly different. For example, FIG. 6 illustrates a small ligand L chemically fused to a larger molecule 615 (e.g., greater that 50 KDa) in view 605. View 610 shows the combination of GPCR bound to the ligand which is chemically fused to the larger molecule 615, and the combined GPCR bound to the ligand (fused to the larger molecule 615) has a longer dwell time (retention time) in the nanochannel 35 as measured by the ammeter 50 (e.g., via the computer 1700) for this particular test solution T1, T2, and/or T3, when voltage is applied by the voltage source 55.

Similarly, the surface charge of the ligand may be modified in a way so that the charge of RL and subsequent retention time is significantly changed. An example may be the fusing of the ligand to a polyelectrolyte such as low molecular weight chitosan (Poly(D-glucosamine)), which has a high positive charge density in low to neutral pH solutions. The high charge density of such a ligand, even if its mass is <5000 Da, would result in a large change in translocation time when bound to the GPCR.

There may be embodiments where the small ligand(s) of interest (e.g., the drug being tested) cannot be modified, such as when the operator is screening a library of molecules (ligands) for potential drugs. In this case, referring to FIG. 7, the operator can preload the receptor with a large and/or charged tracer ligand 715 (for the test solutions T1, T2, and/or T3) in view 705, and screen for small ligand(s) that are able to displace the tracer ligand 715 and thus change the retention time as shown in view 710. An example of such a ligand (large and/or charged tracer ligand 715) may be a low affinity peptide agonist of a GPCR, fused to albumin. For example, the ionic current measured in the nanodevice 100 is lower when the large and/or charged tracer ligand 715 is bound to the GPCR, and the time duration (measured via the ammeter 50) is longer for the large and/or charged tracer ligand 715 bound to the GPCR in the nanochannel 35 (for this test solution T1). This would indicate that the test ligands, which are the small ligands did not replace the large/charged tracer 715 in the nanodevice 100. However, when the ionic current is higher and the time duration in the nanochannel 35 is shorter (measured via the ammeter 50) for test solution T2, this is determines that the small (replacement) ligand has replaced the larger/charged tracer ligand 715 and is bound to the GPCR (in place of the large tracer ligand 715) as shown in view 710; as such, the higher ionic current (e.g., with less of a ionic current drop that for view 705) means that the ligand being tested in test solution T2 successfully binds to the GPCR and is a successful drug candidate via nanodevice 100.

Figure 2:
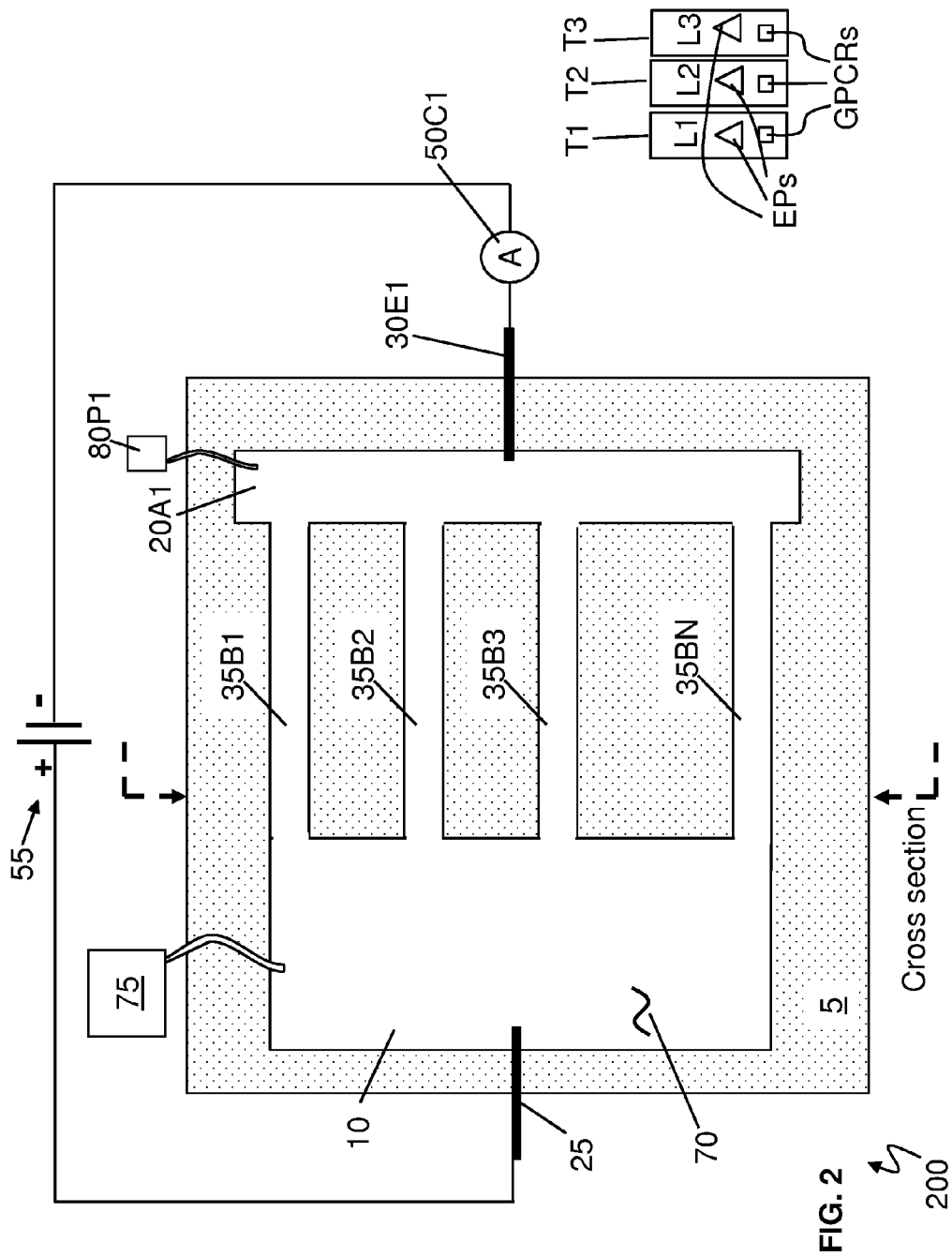
FIG. 2 is a schematic of a top view of a nanodevice according to an embodiment.

In one case with reference to FIG. 8, the nanochannels 35 of nanodevices 100 and 200 may be coated (functionalized) with a coating 805 to selectively interact (e.g., attach/bond) to the desired molecules that translocate through the nanochannels 35, (e.g., reduces the ionic current when the molecule is in the nanochannel 35 and/or increases the time duration in the nanochannel 35 as measured via the ammeter 50). For example, the surface of the nanochannel 35 may be coated with a known ligand of low affinity or moderate affinity (a ligand with a Kd (affinity) of 1-100 μM) (i.e., coating 805), where μM is micromoles. For a particular test solution in the reservoir 10 of the nanodevice 100, 200, binding of receptors to the immobilized ligand coating 805 will retard the mobility of the receptor (GPCR) through the nanochannel 35, increasing their retention times measured via the ammeter 50 (connected to the computer 1700). If a small ligand (e.g., test drug candidate) binds to the receptor (GPCR) before the receptor enters the nanochannel 35, the receptor's binding site is then unavailable for binding to the immobilized ligand (i.e., coating 805) on the inside surface of the nanochannel 35 and thus the receptor will translocate faster (as measured by the ammeter 50 and/or computer 1700) through the nanochannel 35 (by showing a shorter time duration for the drop in ionic current). It is noted that FIG. 8 shows a partial view of the nanodevice 100 and 200. Certain elements are removed so as not to obscure the figure, and it is understood that the respective omitted features are present in the nanodevice 100 and 200 as shown in FIGS. 1 and 2, respectively. For more information regarding functionalization with the coating 805 (and/or coating 905 discussed in FIG. 9), reference can be made to U.S. application Ser. No. 13/439,265 filed Apr. 4, 2012, which is herein incorporated by reference in its entirety.

Figure 9:
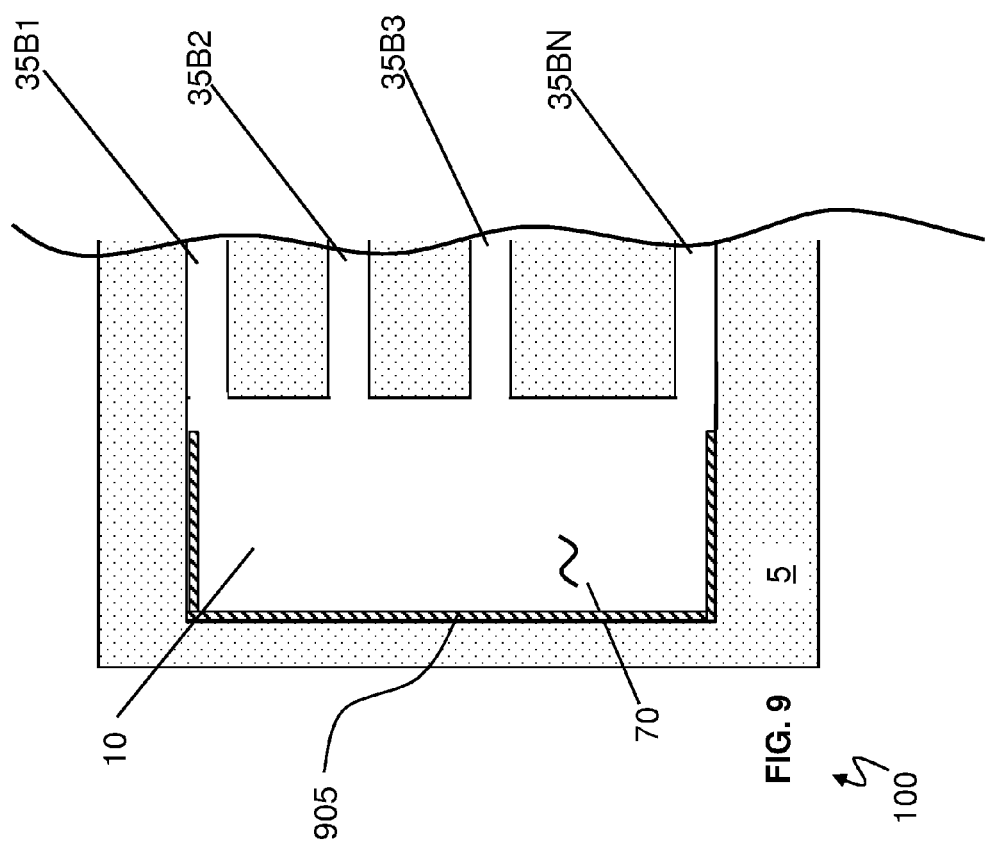
FIG. 9 illustrates a joint reservoir of the nanodevice coated with a coating to selectively interact with desired molecules in test solutions by attaching/bonding to the desired molecules before the desired molecules are able to translocate through the nanochannels according to an embodiment.
Figure 12:
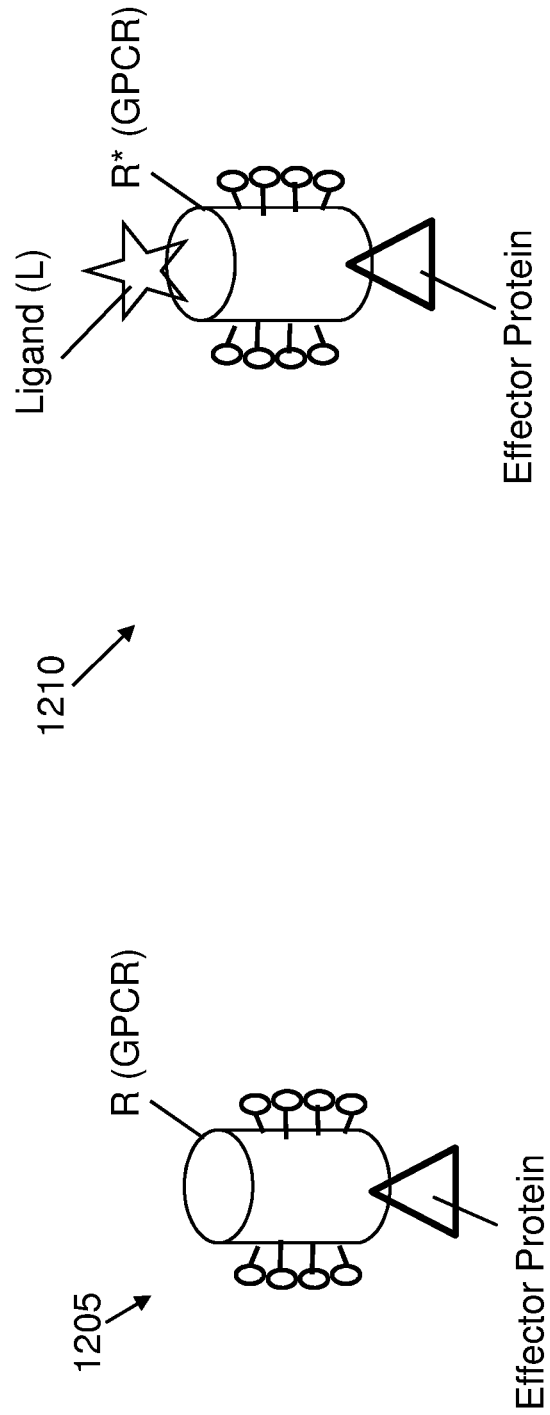
FIG. 12 illustrates a receptor (GPCR) fused directly to an effector protein, where in the inactive state of the receptor, the fusion is in a linear/flexible conformation and when the receptor is activated by a bound ligand, the fusion of the receptor effector protein has a compact state, all of which may be utilized for any test solution as setup for biosensing testing via the nanodevice according to an embodiment according to an embodiment.

Conversely, FIG. 9 illustrates the reservoir 10 of nanodevices 100 and 200 coated with a coating 905 (which may be the same as the coating 805) to selectively interact (e.g., attach/bond) to the desired molecules in the test solutions T1, T2, and/or T3 which prevents the GPCR from moving to and translocating through the nanochannels 35. For example, the reservoir 10 may be coated with a known ligand of low affinity or moderate affinity so that in the absence of binding to another molecule, receptors (GPCR) are bound to the inner surface of the reservoir 10 and are thus unable to enter the nanochannel 35. Upon the binding of another ligand (e.g., the test ligand/test drug) that can displace the immobilized ligand (coating 905) (similar to the small ligand displacing the large/charged tracer ligand 715 in FIG. 7), the RL (i.e., combined GPCR and ligand) is then able to enter and translocate through the nanochannel 35. As such, for this test solution, when the ammeter 50 (connected to the computer 1700) detects an ionic current drop (for a long time duration), the computer 1700/operator determines that this ionic current drop is due to the GPCR and ligand combination translocating through the nanochannel 35, which means the ligand being tested is successful. However, when the ammeter 50 (connected to the computer 1700) detects small ionic current drop (for a small time duration), the computer 1700/operator determines that this ionic current drop is due to (only) the unbound ligand translocating through the nanochannel 35 because the GPCR is bound to the coating 905 in the reservoir 10; the GPCR bound to the coating 905 (i.e., bound to the ligand in the coating 905) does not get displaced by the test ligand for this test solution being tested.

Measuring R Versus R*:

Additional features (e.g., measuring R versus R*) for screening GPCRs in nanochannels involve the detection of receptors in an active state (R*) in the prepared test solutions T1, T2, and T3. In the active state, the GPCR (R*) is able to bind to various effector proteins (EPs), which in the cell (of a human) would result in signaling. In the nanopore environment of the nanodevice 100 (200), the operator can use the activated receptor's (R*) ability to bind to effector proteins (EP) as a tool to resolve a translocating activated receptor, from an inactive receptor via the ammeters 50 (e.g., connected to the computer 1700); this is based on the activated receptor's (R*) bound to effector protein (EP) having a longer time duration for the ionic current drop than the inactive receptor not bound to the effector protein (EP).

For example, if the effector protein EP is large (>50 kDa), then the effector EP may be added to, e.g., the test solution T1 of receptor (GPCR) and ligand(s) because the mass difference of the R*EP complex enables resolution of activated receptor complexes from inactive receptor monomers by measuring the retention time (as determined by the time duration for the change in ionic current when measured by the ammeter 50) in the respective nanochannels 35. For example, when the large effector protein (with a large mass) binds to activated GPCR (which has been activated by binding to the test ligand (L)), the size and mass of the effector protein (EP) is large compared to the diameter (size) of the nanochannel 35 in which the GPCR bound to both the ligand and effector protein (as shown in view 405 and 505 in FIGS. 4 and 5 respectively), and this large effector protein (EP) slows the translocation (movement) of the GPCR through nanochannel 35 (i.e., slows the travel from the reservoir 10 to the respective individual reservoir 20 (e.g., reservoir 20A1). As such, the ammeter 50 (e.g., ammeter 50C1) connected to the computer 1700 determines that the GPCR bound to both the ligand and effector protein (in view 405 and 505) has a longer time duration of blocking the nanochannel 35B1 (and the ionic current drops (even) lower for test solution T1) as compared to the time duration (and ionic current drop) for the GPCR (not bound to the ligand and effector protein EP in, e.g., test solution T2) translocating through the nanochannels 35. The computer 1700 and/or operator determines that the test solution T1 had ligands which bound and activated the GPCR because the effector proteins (large in size and mass) were able to bind to the activated GPCR (thus increasing the time duration in the nanochannel 35 and causing the (large) ionic current drop), while the GPCR with different ligands in the test solution T2 did not cause the same.

Referring to FIG. 10 as another feature (in an example test solution T1), when the effector protein (EP) to be used is small (<10 kDa), then the effector protein EP may be fused (i.e., covalently linked together) to a large molecule 615 (in view 1005) to enhance the mass change of the R*EP complex in view 1010. View 1010 shows that the ligand (L) has bound to and activated the GPCR (e.g., any receptor), and in turn, the effector protector EP fused to the large molecule 615 is (now) bound to the activated GPCR. The ammeter 50 (connected to the computer 1700) determines that the activated GPCR bound to the (small) ligand and bound to the effector protein (fused to the large molecule 615) translocates slowly through the particular nanochannel 35 (e.g., nanochannel 35B1) because the ionic current drop is for a long time duration in, e.g., test solution T1 as compared to test solutions T2 and T3 (in which the effector protein EP did not bind to the GPCR because their ligands did not activate the GPCR in test solutions T2 and T3).

Similarly, the effector protein (EP) may be functionalized with charge(s) 1115 (in FIG. 11) so that the charge of the R*EP complex (which is, e.g., the activated GPCR bound to the effector protein along with the ligand) is significantly different than the charge of the inactive receptor (e.g., the GPCR which is not bound to the effector protein and not bound to the ligand), and so that the two states can be resolved by measuring the translocation time by the ammeter 50 (connected to the computer 1700). In view 1105, FIG. 11 shows the effector protein (EP) with positive charges 1115 (charges can be negative charges in another case), and the effector protein with charges 1115 can be bound to the GPCR (which is bound to and activated by the ligand (L)) as shown in view 1110.

Instead of adding the effector protein EP to the receptor/ligand solution (such as test solution T1), the nanochannel 35 itself may be coated (with coating 805 as shown in FIG. 8) with an effector protein EP of interest. In this case, R* (e.g., activated GPCR) is able to bind to the immobilized effector protein (i.e., the coating 805) and is thus retarded (slowed down) within the nanochannel 35, greatly increasing the translocation time of R* (which combines with and is slowed down by the coating 805 of the effector protein EP in the nanochannel 35, where the GPCR is activated by and bound to the ligand) in comparison to R (i.e., the GPCR that is not activated by the ligand). As discussed herein, the two different translocation times for R* and R are determined by the extended/large time duration in which the ionic current drops while the activated GPCR (continuously binds with the coating 805 of effector proteins as the GPCR travels through the nanochannel 35) as compared to the small/shorter time duration of the unactivated GPCR (which is not bound to the ligand and thus does not bind to the immobilized effector protein in the coating 805 for this particular test solution, e.g., test solution T2).

In one case (for test solution T1), the reservoir 10 may also be coated with effector protein (EP) (i.e., coating 905 in FIG. 9) so that R* (activated GPCR) binds and is inhibited from entering the nanopore/nanochannel 35, with only R (unactivated GPCR) being able to translocate through the nanochannel 35 to have the ionic current measured via ammeter 50 (connected to the computer 1700). For example, the activated GPCR (bound to the ligand) is bound to the coating 905 of effector protein (EP) such that the activated GPCR cannot move to the opening of the nanochannel 35 to translocate to the (respective) individual reservoir 20; since GPCR does not translocate through nanochannel 35 (i.e., does not inhibit/partially block) the flow of ionic current through the respective nanochannel 35, the ionic current (measured by the ammeter 50 connected to the computer 1700) does not drop when testing test solution T1, which means that the ligands (i.e., drug being tested) binds to and activate the GPCR. However, when the ligand, e.g., in test solution T2 does not bind to and activate the GPCR, the GPCR translocates through the nanochannel 35 from the reservoir 10 to the respective individual reservoir 20, and the drop in measured ionic current (via ammeter 50 connected to computer 1700) is detected, which indicates that the ligand did not bind to and activate the GPCR in test solution T2.

In another case, the receptor of interest (e.g., GPCR) can be directly modified to facilitate the detection of R* versus R. Such an example would be to fuse (covalently link) the receptor (GPCR) directly to an effector protein EP as shown in view 1205 of FIG. 12. In the inactive state, the fusion would be in a linear/flexible conformation (i.e., the two fused elements can move independently, tethered to each other only through the covalent linkage) that would result in a particular/predefined translocation time (e.g., 2 seconds) for the view 1205. When activated as shown in view 1210, however, the R*EP fusion would adopt a more compact state (i.e., a smaller size) due to the binding of the EP to R* (the two fused elements are now locked together through the covalent linkage and other interactions between other parts of the molecule), resulting in a different translocation time.

Figure 13:
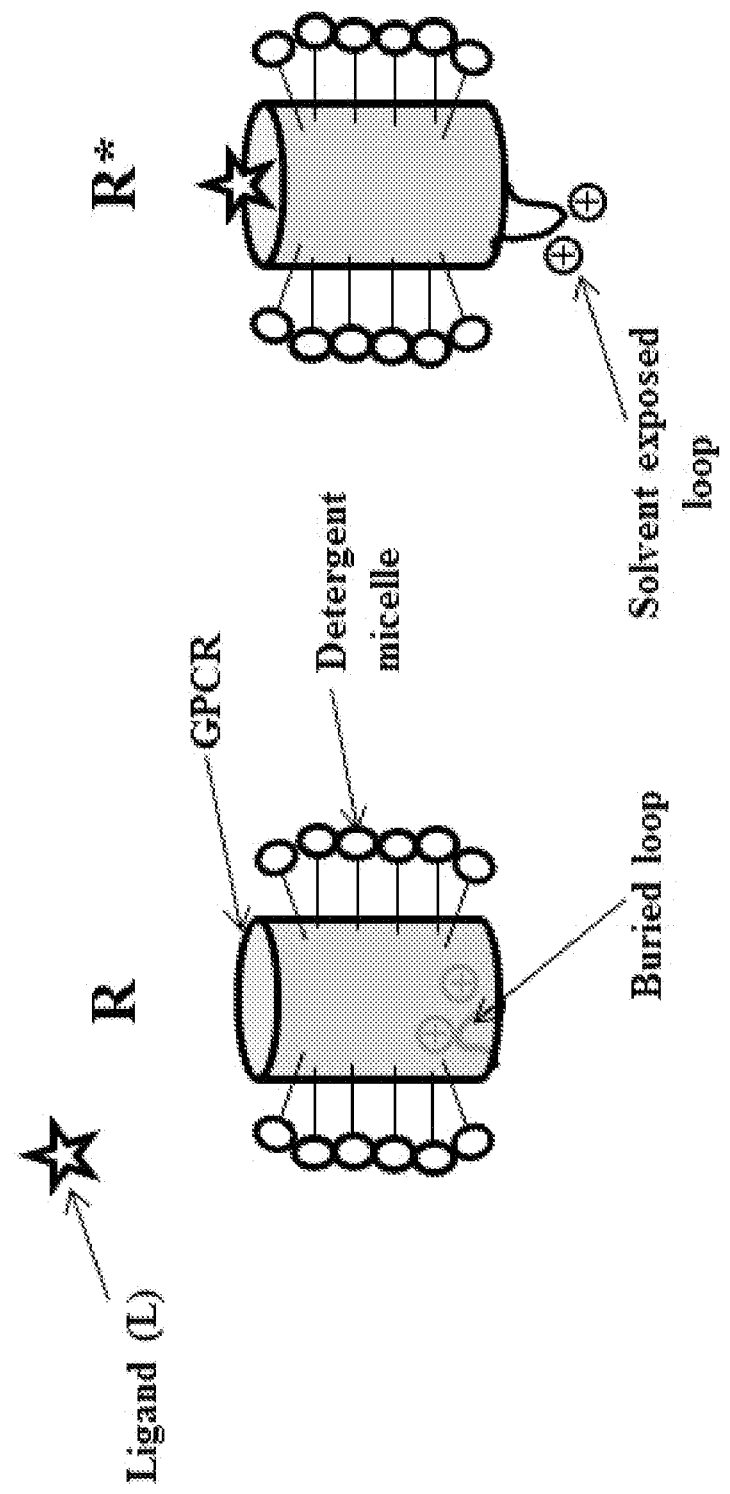
FIG. 13 illustrates receptor modification where charged amino acids are buried in the structure or buried in the detergent micelle when the receptor is in the inactive state, and illustrates upon activation by the ligand, the activated receptor changes shape to expose the charged amino acids on the surface of the molecule, all of which may be utilized for any test solution as setup for biosensing testing via the nanodevice according to an embodiment according to an embodiment.

As shown in FIG. 13, another receptor modification (of the GPCR) may be the introduction of charged amino acids that are buried in the structure or buried in the detergent micelle when the receptor is in the inactive state. Upon activation, however, the receptor changes shape leading to the exposure of the charged amino acids on the surface of the molecule leading to a change in the translocation time of R* (activated receptor).

Further definitions and examples are provided below.

Ligand: A ligand may be any small molecule, peptide, protein, sugar, lipid, small molecule library, peptide library, protein library that binds to a given receptor at the orthosteric binding site, at an allosteric binding site or any other binding sites in the receptor protein.

Examples of Effector Proteins (EP):

G-alpha peptides: GPCRs send signals into the cells by interacting and modifying the states of heterotrimeric G proteins. G alpha subunits are one component of the heterotrimer. Peptides derived from the C-Terminus of the G-alpha subunit can specifically interact with the intracellular side of activated GPCRs.

In one case, one can use these peptides (G-alpha peptides) to functionalize the nanopore/nanochannel 35 via coating 805 (of peptides), so that the translocation of activated GPCRs through the nanopore/nanochannel 35 is retarded by interactions with the immobilized peptides of the coating 805. Also, note that these peptides can also be fused (i.e., covalently linked) to GPCRs to detect activation.

More information regarding binding peptides (e.g., EP) to GPCR can be found in the following herein incorporated by reference. Gilchrist, A., Bunemann, M., Li, A., Hosey, M. M., and Hamm, H. E. (1999) J Biol Chem 274, 6610-6616. Gilchrist, A., Vanhauwe, J. F., Li, A., Thomas, T. O., Voyno-Yasenetskaya, T., and Hamm, H. E. (2001) J Biol Chem 276, 25672-25679. Van Eps, N., Anderson, L. L., Kisselev, O. G., Baranski, T. J., Hubbell, W. L., and Marshall, G. R. (2010) Biochemistry 49, 6877-6886. Scheerer, P., Park, J. H., Hildebrand, P. W., Kim, Y. J., Krauss, N., Choe, H. W., Hofmann, K. P., and Ernst, O. P. (2008) Nature 455, 497-502

Other G proteins (such as G protein heterotrimers): the operator can coat (using the coating 805) the nanopore/nanochannel 35 with the alpha, gamma, and beta G protein subunits (the heterotrimer). More information regarding the crystal structure can be found in the following herein incorporated by reference: Rasmussen, S. G., DeVree, B. T., Zou, Y., Kruse, A. C., Chung, K. Y., Kobilka, T. S., Thian, F. S., Chae, P. S., Pardon, E., Calinski, D., Mathiesen, J. M., Shah, S. T., Lyons, J. A., Caffrey, M., Gellman, S. H., Steyaert, J., Skiniotis, G., Weis, W. I., Sunahara, R. K., and Kobilka, B. K. (2011) Nature 477, 549-555.

GPCR binding antibodies: recently, some antibodies and nanobodies have been produced that bind to certain GPCRs and stabilize the GPCRs in the active state. These were produced for crystallization, but in the present disclosure the operator can coat (via the coating 805) the nanopore/nanochannel 35 with an antibody that either recognizes activated GPCR, or recognizes inactivated GPCR, to increase the resolution of our measurements in the nanodevice 100 (200). More information regarding GPCR binding antibodies can be found in the following herein incorporated by reference: Rasmussen, S. G., Choi, H. J., Fung, J. J., Pardon, E., Casarosa, P., Chae, P. S., Devree, B. T., Rosenbaum, D. M., Thian, F. S., Kobilka, T. S., Schnapp, A., Konetzki, I., Sunahara, R. K., Gellman, S. H., Pautsch, A., Steyaert, J., Weis, W. I., and Kobilka, B. K. (2011) Nature 469, 175-180. Hino, T., Arakawa, T., Iwanari, H., Yurugi-Kobayashi, T., Ikeda-Suno, C., Nakada-Nakura, Y., Kusano-Arai, O., Weyand, S., Shimamura, T., Nomura, N., Cameron, A. D., Kobayashi, T., Hamakubo, T., Iwata, S., and Murata, T. (2012) Nature 482, 237-240.

GPCR dimerization: Some GPCRs can be active in dimeric or oligomeric states. In the test setup of the present disclosure, the receptors are solubilised, and the nanodevice 100 can measure differences in oligomeric states.

β-arrestin interactions with GPCRs: β-arrestins bind specifically to active GPCRs. Binding of β-arrestin to the active GPCR results in a significant size increase, enabling distinction between active and inactive GPCRs. β-arrestin can be utilized (as the coating 805) to coat the nanochannel 35, particularly binding to active GPCRs and slowing passage through the nanochannel 35. Alternately, β-arrestin and GPCRs could be mixed prior to passing through the nanochannel 35. Active GPCRs could be distinguished by the increased translocation time due to the size of the complex formed between β-arrestin and the GPCR. More information of regarding β-arrestin binding to GPCRs is found in the following which is herein incorporated by reference: Vishnivetskiy, S. A., Gimenez, L. E., Francis, D. J., Hanson, S. M., Hubbell, W. L., Klug, C. S., and Gurevich, V. V. (2011) J Biol Chem 286, 24288-24299. Han, M., Gurevich, V. V., Vishnivetskiy, S. A., Sigler, P. B., and Schubert, C. (2001) Structure 9, 869-880.

GRK interactions with GPCRs: G-protein coupled receptor kinases (GRKs) are kinases that specifically phosphorylate active GPCRs. Recent structural evidence shows that GRKs interact directly with GPCRs in order to conduct GPCR phosphorylation. Inactive GPCRs will not bind GRKs, while GRKs can interact with active GPCRs. In the present disclosure, use of this interaction can be by coating the nanochannel 35 with GRKs, which could interact with active GPCRs, increasing the translocation time with respect to inactive GPCRS that do not interact with GRKs. Crystal structure of GRK6 and the recognition site for GPCRs is discussed in the following which is herein incorporated by reference: Boguth, C. A., Singh, P., Huang, C. C., and Tesmer, J. J. (2010) The EMBO journal 29, 3249-3259.

Further embodiments employing the nanodevice 100 (200) are discussed below.

In the present disclosure, the operator can use pH manipulation of the electrolyte solution 70 in the reservoir 10, nanochannels 35, and individual reservoirs 20. Proteins can exhibit positive, negative, or zero net charge depending on the pH of the electrolyte solution. The net charge will affect which proteins translocate through the nanochannel 35 (e.g. negatively charged proteins only translocate through the nanochannel 35 when the opposite side contains the cathode). The pH at which a protein has zero net charge is called the isoelectric point (pI). Different proteins have different isoelectric points (pI), which may shift upon binding to a ligand. Accordingly, the electrolyte solution 70 can be created to have a desired pH level such that only protein-ligand complexes translocate through the nanochannel 35; therefore, an ionic current drops would represent translocation of bound protein-ligand complexes. In the case where protein-ligand complexes and unbound proteins and/or ligands translocate through the channel, the individual entities, and combinations thereof, may be electrically distinguishable as measurable parameters (e.g., number of events, speed of translocation, ionic current drop) will be influenced by the isoelectric point (i.e. net charge). When modifying the pH value of the electrolyte solution 70, the following may be considered: the stability of the proteins at different pH levels; the predictability of the pI for protein-ligand complexes (knowing what pH to use, such as a pH value between 4 and 9 in which most proteins are stable); the effect of the detergent (which may also be referred to as a surfactant) on net charge; the electrostatic interaction with the wall (of the nanochannel 35); and limiting both unbound proteins and ligands from translocation, where it is desired to have only protein-ligand complexes translocate. For example, bound proteins and unbound proteins straddle the isoelectric point. This results in only bound proteins being translocated (where the measurable is an event occurring). As another example, bound proteins and unbound proteins are both above or below the isoelectric point but to different extents (different isolelectric points). This results in both types translocating but at different speeds (where the measurable is the number of translocation events or speed of event).

In one embodiment, one can manipulate the concentration (ionic strength) of the electrolyte solution 70. If the ionic strength of the electrolyte solution 70 (buffer solution) is low enough, the net charge of a protein will contribute to the change in ionic current during translocation, as ions of opposite polarity associate with the charged protein. Assuming proteins, ligands, and protein-ligand complexes have different net charges (in one case in the present disclosure), embedded electrodes 30 can measure the change in current in the longitudinal direction or across the nanochannel 35 (transverse direction) using embedded electrodes. These measurements of the ionic current (via an ammeter 50) are based on net charge magnitudes and distribution of entities.

In one embodiment, the nanodevice 100 may include capacitive sensing via embedded electrode pair 1405D1 through embedded electrode pair 1405D4 as shown in FIG. 14. Rather than (only) measuring changes in ionic current, changes in voltage or electric field due to the net charges of the proteins and ligands can also be utilized for the detection of bound protein-ligand complexes in the nanodevice 100 shown in FIG. 14. Due to the net charges, embedded electrodes 1405D1 through 1405D4 can measure the change in capacitance or electric field for individual translocation events across the nanochannel 35 (transverse direction) via respective capacitance meter 1410F1 through capacitance meter 1410F4. Additionally, as discussed above, surface functionalization is used to cause binding of the protein and ligand at the nanochannel 35 surface (e.g., as shown in FIG. 8). In this instance, there is a gradual change in capacitance across the nanochannel 35 until saturation is reached and the change in capacitance becomes permanent. Otherwise, the two embedded electrodes can be fabricated/oriented such that they act as a capacitor measuring voltages in the longitudinal direction. The capacitance is based on the magnitudes and distribution of the net charges within the protein/ligand, and the capacitance may be measured by the respective capacitance meters 1410 for the respective nanochannels 35. FIG. 14 only shows a simplified version of the nanodevice 100 with certain elements omitted so as not to obscure the figure. Although not shown for the sake of brevity, it is contemplated that FIG. 14 also includes the elements described in FIG. 1.

Figure 15:
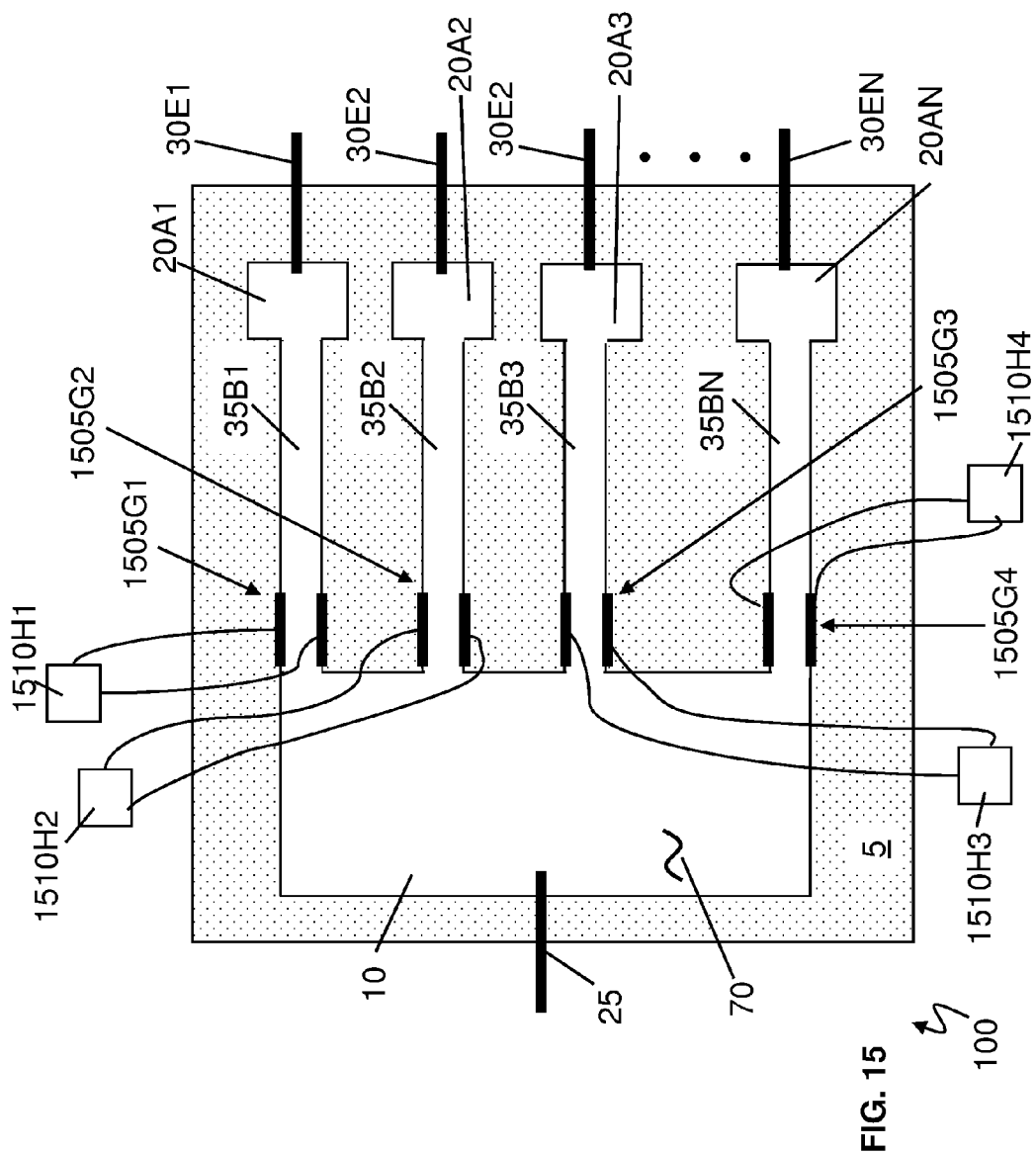
FIG. 15 is a schematic of the nanodevice with gate electrodes to control the surface charge inside the nanopore/nanochannel according to an embodiment.

In one embodiment, gate electrodes can be utilized to control the surface charge inside the nanochannel 35 in FIG. 15. Gate electrodes 1505G1 through 1505G4 are respectively in nanochannels 35B1 through 35Bn. Each gate electrode 1505G1 through 1505G4 is respectively connected to its own voltage source 1510H1 through 1510H4. Depending on the surface charge within the nanochannel 35, proteins and ligands will or will not translocate through the nanochannel 35. The surface charge can be modified inside the nanochannel 35 to promote translocation events of bound protein-ligand complexes. The surface charge in the nanochannel 35 can limit both unbound proteins and ligands from translocation. For example, when a positive voltage is applied by the respective voltage sources 1510, each nanochannel 35 may have a positive electric field (e.g., pointing to the right). The positive electric field in each nanochannel 35 attracts negatively charged molecules while repelling positively charged molecules from entering into the nanochannel 35. It is understood that a negative voltage would produce a negative electric field (e.g., pointing to the left), and the negative electric field attracts positively charged molecules into the nanochannel 35 while repelling negatively charged molecules.

In one case, the ligand can be positively charged, when there is a negative electric field in each of the nanochannels 35 as generated by negative voltage applied by the respective voltage sources 1510 through respective gate electrodes 1505. When the positively charged ligand binds with the GPCR, the combined ligand and GPCR (having a net positive charge) translocates through the nanochannel 35 in a shorter time duration than unbound GPCRs, which is measured by the ammeter 50 (connected to the computer 1700). When the negative electric field is applied, (positively charged) ligands are determined to be successful drug candidates when the ammeter 50 connected to the computer 1700 measures ionic current blockages for (only) a short time duration. This indicates that the positively charged ligand has bound to the GPCR, and the combined ligand and GPCR are quickly swept through the nanochannel 35.

The same applies by analogy for negatively charged ligands when a positive electric field is generated by the positive voltage (of the respective voltage sources 1510). In this case, when the negatively charged ligand binds with the GPCR, the combined ligand and GPCR (having a net negative charge) translocates through the nanochannel 35 in a shorter time duration than unbound GPCRs, which is measured by the ammeter 50 (connected to the computer 1700). When the positive electric field is applied, (negatively charged) ligands are determined to be successful drug candidates when the ammeter 50 connected to the computer 1700 measures ionic current blockages for (only) a short time duration. This indicates that the negatively charged ligand has bound to the GPCR, and the combined ligand and GPCR are quickly swept through the nanochannel 35.

Although FIG. 15 illustrates one example for the location of the gate electrodes 1505, it is understood that the gate electrodes may be positioned in varied location within the nanochannel 35. For example, the gate electrodes 1505 may be at the mouth of the nanochannel 35 (as currently shown in FIG. 15), at the middle of the nanochannel 35, and/or at the tail end of the nanochannel 35 (e.g., near the individual reservoirs 20).

Figure 16:
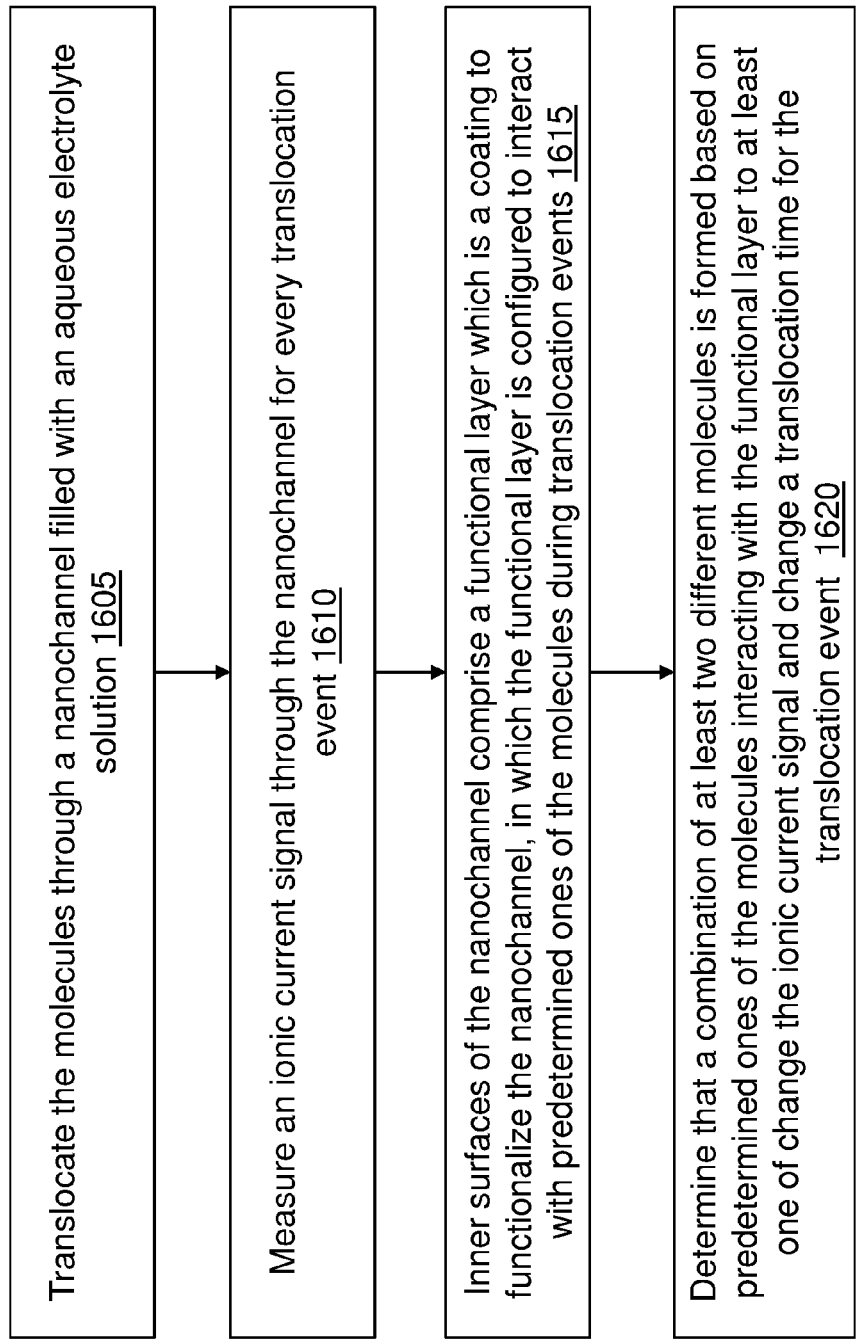
FIG. 16 is a flow diagram of a method utilizing the nanodevice to distinguish molecules (e.g., proteins, ligands, effector proteins, large molecules, and combinations, etc.) with different structures to determine when the protein binds with a ligand according to an embodiment.

Referring to FIG. 16, a flow diagram 1600 of a method for the nanodevice 100, 200 is provided for distinguishing molecules (e.g., proteins, ligands, effector proteins, large molecules, combined protein and ligand, etc.) with different structures to determine when the protein (e.g., GPCR) binds with a ligand (e.g., the drug being tested) and/or when the protein does not bind with ligand (e.g., for a particular test solution) according to an embodiment. Note that reference can be made to FIGS. 1-15 and 17 discussed herein. The molecules in test solutions T1, T2, and T3 (which may include the various scenarios as discussed herein) being tested are prepared and poured/pumped into the reservoir 10 (during their respective test run) when each test solution is individually tested in the nanodevice 100 (or nanodevice 200) and then flushed for the next test solution as discussed herein.

When a voltage is supplied from the voltage source 55, the molecules translocate molecules through a nanochannel (e.g., nanochannels 35) filled with an aqueous electrolyte solution (e.g., aqueous electrolyte solution 70) at block 1605.

The respective ammeters 50C1 through 50CN (connected to the computer 1700) measure an (individual) ionic current signal through the nanochannel(s) (e.g., through each individual nanochannel 35B1 through 35Bn) for every event at block 1610. Not that an event includes a translocation event and binding event. A binding event is when the ligand binds with a protein (e.g., such as a mutated protein (GPCR)).

At block 1615, the inner surfaces of the nanochannel(s) 35 comprise a functional layer which is a coating 805 to functionalize the nanochannel(s) 35, in which the functional layer is configured to interact with predetermined ones of the molecules during translocation events as discussed herein.

At block 1620, the computer 1700 (connected to the respective ammeters 50) and/or user (viewing the ammeter 50 and computer 1700) determines that a combination of at least two different molecules is formed (e.g., the ligand is bound to the GPCR) based on predetermined ones of the molecules interacting with the functional layer to at least one of change the ionic current signal and change a translocation time for the translocation event (measured by and displayed on the ammeter 50 connected to the computer 1700).

In the method, the ionic current signal is ionic current caused by ions translocating through (at least part of) the nanochannel 35 induced by an applied voltage (by the voltage source 55) in a longitudinal direction of the nanochannel 35. The translocation event is defined by the following: a molecule (which may be a combination of molecules, such as the protein (GPCR) ligand complex/combination) approaching one end of the nanochannel 35 connected to a first nanofluidic reservoir (e.g., joint reservoir 10) with the nanochannel 35 being unblocked (at the entrance or exit); the molecule entering the nanochannel 35 (from the joint reservoir 10); the molecule moving through the nanochannel blocking the respective nanochannel 35 to an extent (e.g., may be partially blocked and some molecules (and/or combination of molecules) block the nanochannel more than other molecules); the molecule exiting the nanochannel at an opposite end of the nanochannel 35 connected to a second nanofluidic reservoir (e.g., connected to any one of the individual reservoirs 20A1 through 20AN); and the molecule moving away from the nanochannel 35 into the second nanofluidic reservoir leaving the nanochannel 35 unblocked again.

In the method, the molecules may be chosen from a group comprising proteins, electrically charged molecules, electrically neutral molecules, organic compounds, inorganic compounds, effector proteins, and combinations thereof. The proteins may be G-protein coupled receptors (GPCR). At least two different molecules engage in binding reactions to form the combination before translocating through the nanochannel 35 (e.g., the ligand can bind with the GPCR in the test solution and/or in the joint reservoir 10 before entering a particular nanochannel 35). Based on the translocation events occurring in multiple nanochannels 35A1 through 35An formed in a substrate 5, longitudinal directions of the multiple nanochannels 35 are parallel to the plane of the substrate 5 that the nanochannels 35 are integrated into.

The method in which a portion of a nanochannel surface of the nanochannels 35 is an electrode (e.g., embedded electrodes 1405 form part of the nanochannel surface for nanochannels 35B1 through 35BN).

The method in which the functional layer (coating 805) is a direct self-assembled monolayer, the functional layer is an oxide layer, the functional layer is an organic layer, and/or the functional layer is an inorganic layer.

The method in which the same voltage amount is applied (by the voltage source 55) to each of the multiple nanochannels 35 through electrodes 30 connected to reservoirs at both ends (e.g., joint reservoir 10 at one end and individual reservoirs 20 at the other end) of each of the multiple nanochannels 35.

In the method, a modulation signal of the ionic current signal comprises at least one of an ionic current drop, an ionic current increase, and a combination thereof during the translocation events. The modulation ionic current signal is the change in the time and/or amplitude of the measured ionic current when the molecule translocate through the nanochannel 35 during each individual translocation event. A time duration of the modulation signal of the ionic current signal is measured (via ammeter 50 connected to the computer 1700), and an amplitude of the modulation signal of the ionic current signal is measured (via ammeter 50 connected to the computer 1700). Also, a translocation event frequency of the modulation signal of the ionic current signal is measured (via ammeter 50 connected to the computer 1700) to determine a number of occurrences of the translocation events. The method in which at least two different modulation signals (of ionic current) for two subsequent translocation events represent different molecular states of translocating molecules. The distributions of measured modulation signals over a defined period of time are statistically analyzed (via the computer 1700) to determine a statistical distribution of the corresponding various molecular states of all the molecules that translocated during the defined period of time.

Further, information regarding extracting the GPCR from a biological environment to a solution is discussed in the review of detergents solubilization of membrane proteins Prive, G. G. Detergents for the stabilization and crystallization of membrane proteins. *Methods* 41, 388-397, (2007) (incorporated herein by reference). Further, papers describing the stabilization of GPCRs are herein incoporated by refence: Standfuss, J. et al. Crystal structure of a thermally stable rhodopsin mutant. *J. Mol. Biol.* 372, 1179-1188, (2007). Magnani, F., Shibata, Y., Serrano-Vega, M. J. & Tate, C. G. Co-evolving stability and conformational homogeneity of the human adenosine A2a receptor. *Proc. Natl. Acad. Sci. U.S.A.* 105, 10744-10749, (2008). Roth, C. B., Hanson, M. A. & Stevens, R. C. Stabilization of the human beta2-adrenergic receptor TM4-TM3-TM5 helix interface by mutagenesis of Glu122(3.41), a critical residue in GPCR structure. J. Mol. Biol. 376, 1305-1319, (2008). Sarkar, C. A. et al. Directed evolution of a G protein-coupled receptor for expression, stability, and binding selectivity. *Proc. Natl. Acad. Sci. U.S.A.* 105, 14808-14813, (2008). Serrano-Vega, M. J., Magnani, F., Shibata, Y. & Tate, C. G. Conformational thermostabilization of the beta1-adrenergic receptor in a detergent-resistant form. *Proc. Natl. Acad. Sci. U.S.A.* 105, 877-882, (2008). Shibata, Y. et al. Thermostabilization of the neurotensin receptor NTS1. J. Mol. Biol. 390, 262-277, (2009). Dodevski, I. & Pluckthun, A. Evolution of three human GPCRs for higher expression and stability. *J. Mol. Biol.* 408, 599-615, (2011). Robertson, N. et al. The properties of thermostabilised G protein-coupled receptors (StaRs) and their use in drug discovery. *Neuropharmacology* 60, 36-44, (2011). Chen, K. Y., Zhou, F., Fryszczyn, B. G. & Barth, P. Naturally evolved G protein-coupled receptors adopt metastable conformations. *Proc. Natl. Acad. Sci. U.S.A.* 109, 13284-13289, (2012). Schlinkmann, K. M. et al. Maximizing detergent stability and functional expression of a GPCR by exhaustive recombination and evolution. *J. Mol. Biol.* 422, 414-428, (2012). Schlinkmann, K. M. et al. Critical features for biosynthesis, stability, and functionality of a G protein-coupled receptor uncovered by all-versus-all mutations. *Proc. Natl. Acad. Sci. U.S.A.* 109, 9810-9815, (2012).

FIG. 17 illustrates an example of a computer 1700 (e.g., as part of a computer setup for testing and analysis) having capabilities, which may be included in exemplary embodiments. Various methods, procedures, modules, flow diagrams, tools, applications, circuits, elements, and techniques discussed herein may also incorporate and/or utilize the capabilities of the computer 1700. Moreover, capabilities of the computer 1700 may be utilized to implement features of exemplary embodiments discussed herein. One or more of the capabilities of the computer 1700 may be utilized to implement, to connect to, and/or to support any element discussed herein (as understood by one skilled in the art) in FIGS. 1-16. For example, the computer 1700 which may be any type of computing device and/or test equipment (including ammeters, capacitance meters, voltage meters, multimeters, voltage sources, connectors, etc.). Input/output device 1770 (having proper software and hardware) of computer 1700 may include and/or be coupled to the nanodevice discussed herein via cables, plugs, wires, electrodes, etc. Also, the communication interface of the input/output devices 1770 comprises hardware and software for communicating with, operatively connecting to, reading, displaying, and/or controlling voltage sources, capacitance meters, voltage meters, ammeters, ionic current (signals), electric fields, etc., as discussed herein. The user interfaces of the input/output device 1770 may include, e.g., a track ball, mouse, pointing device, keyboard, touch screen, etc., for interacting with the computer 1700, such as inputting information, making selections, independently controlling different voltages sources, and/or displaying, viewing and recording ionic current (signal) for each molecule, biomolecules, combined molecules (e.g., ligand bound to GPCR), etc.

Generally, in terms of hardware architecture, the computer 1700 may include one or more processors 1710, computer readable storage memory 1720, and one or more input and/or output (I/O) devices 1770 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 1710 is a hardware device for executing software that can be stored in the memory 1720. The processor 1710 can be virtually any custom made or commercially available processor, a central processing unit (CPU), a data signal processor (DSP), or an auxiliary processor among several processors associated with the computer 1700.

The computer readable memory 1720 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 1720 may incorporate electronic, magnetic, optical, and/or other types of storage media. Note that the memory 1720 can have a distributed architecture, where various components are situated remote from one another, but can be accessed by the processor 1710.

The software in the computer readable memory 1720 may include one or more separate programs, each of which comprises an ordered listing of executable instructions for implementing logical functions. The software in the memory 1720 includes a suitable operating system (O/S) 1750, compiler 1740, source code 1730, and one or more applications 1760 of the exemplary embodiments. As illustrated, the application 1760 comprises numerous functional components for implementing the features, processes, methods, functions, and operations of the exemplary embodiments. The application 1760 of the computer 1700 may represent numerous applications, agents, software components, modules, interfaces, controllers, etc., as discussed herein but the application 1760 is not meant to be a limitation. The application 1760 may be a source program, executable program (object code), script, or any other entity comprising a set of instructions to be performed.

The I/O devices 1770 may include input devices (or peripherals) such as, for example but not limited to, a mouse, keyboard, scanner, microphone, camera, etc. Furthermore, the I/O devices 1770 may also include output devices (or peripherals), for example but not limited to, a printer, display, etc. Finally, the I/O devices 1770 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 1770 also include components for communicating over various networks, such as the Internet or an intranet. The I/O devices 1770 may be connected to and/or communicate with the processor 1710 utilizing Bluetooth connections and cables (via, e.g., Universal Serial Bus (USB) ports, serial ports, parallel ports, FireWire, HDMI (High-Definition Multimedia Interface), etc.).

The application 1760 can be embodied in any computer-readable medium 1720 for use by or in connection with an instruction execution system, apparatus, server, or device, such as a computer-based system, processor-containing system, or other system that can fetch the instructions from the instruction execution system, apparatus, or device and execute the instructions. In the context of this document, a "computer-readable storage medium" can be any means that can store, read, write, communicate, or transport the program for use by or in connection with the instruction execution system, apparatus, or device. The computer readable medium can be, for example but not limited to, an electronic, magnetic, optical, or semiconductor system, apparatus, or device.

It is understood that the computer 1700 includes non-limiting examples of software and hardware components that may be included in various devices, servers, and systems discussed herein, and it is understood that additional software and hardware components may be included in the various devices and systems discussed in exemplary embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for determining an association of molecules with different structures, the method comprising:
    translocating the molecules partially or entirely through one or more nanochannels filled with an electrolyte solution based on an electric potential difference applied in a longitudinal direction of the one or more nanochannels;
    measuring one or more electrical signals through, across, or both through and across the one or more nanochannels for every event, the event being a translocation event, a binding event, or both the translocation event and the binding event; and
    determining that at least two different molecules have combined into a combination based on a change in the one or more electrical signals, a change in translocation time for the translocation event, or both a change in the one or more electrical signals and in the translocation time for the translocation event;
    wherein the proteins are G-protein coupled receptors.

2. The method of claim 1, wherein the translocation event is defined by the following:
    a molecule approaching a first end of a nanochannel connected to a first nanofluidic reservoir with the nanochannel being unblocked;
    the molecule entering the nanochannel;
    the molecule moving through the nanochannel blocking the nanochannel to an extent;
    the molecule exiting the nanochannel at a second end of the nanochannel connected to a second nanofluidic reservoir; and
    the molecule moving away from the nanochannel into the second nanofluidic reservoir leaving the nanochannel unblocked again.

3. The method of claim 1, wherein the binding event is defined by the following:
    a molecule approaching a first end of a nanochannel connected to a first nanofluidic reservoir with the nanochannel being unblocked;
    the molecule entering the nanochannel;

the molecule moving across the nanochannel blocking the nanochannel to an extent; and the molecule binding to another molecule fixed at a nanochannel surface.

4. The method of claim 1, wherein the at least two different molecules engage in binding interactions to form the combination before translocating through the one or more nanochannels.

5. The method of claim 1, wherein based on translocation events occurring in multiple nanochannels formed in a substrate, longitudinal directions of the multiple nanochannels are parallel to the plane of the substrate that the multiple nanochannels are integrated into; and wherein a voltage is applied to each of the multiple nanochannels through electrodes connected to reservoirs at both ends of each of the multiple nanochannels.

6. The method of claim 1, wherein one or more portions of one or more nanochannel surfaces are electrodes.

7. The method of claim 1, wherein one or more inner surfaces of the one or more nanochannels include functional layers configured to interact with predetermined molecules during the translocation event, during wetting the one or more inner surfaces, or during both the translocation event and wetting the one or more inner surfaces.

8. The method of claim 7, wherein it is determined that a combination of at least two different molecules is formed based on the predetermined molecules interacting with the functional layers to change the one or more electrical signals, change the translocation time for the translocation event, or change both the one or more electrical signals and the translocation time for the translocation event.

9. The method of claim 7, wherein the functional layers is at least one of a direct self-assembled monolayer, an oxide layer, an organic layer, and an inorganic layer.

10. The method of claim 1, wherein the one or more electrical signals originate from at least one of capacitance, ionic current, tunneling current, electric field, and electric potential.

11. The method of claim 1, wherein a modulation signal of the one or more electrical signals comprises an ionic current or voltage drop, an ionic current or voltage increase, or a combination thereof during the translocation event; and wherein at least one of a time duration of the modulation signal of the one or more electrical signals is measured, and an amplitude of the modulation signal of the one or more electrical signals is measured.

12. The method of claim 11, wherein a translocation event frequency of the modulation signal of the one or more electrical signals is measured to determine a number of occurrences of the translocation event.

13. The method of claim 11, wherein at least two different modulation signals for two subsequent translocation events represent different molecular states of translocating molecules.

* * * * *